United States Patent
Yen et al.

(10) Patent No.: US 10,347,846 B2
(45) Date of Patent: Jul. 9, 2019

(54) ORGANIC COMPOUND FOR ORGANIC EL DEVICE AND USING THE SAME

(71) Applicants: Feng-Wen Yen, Taipei (TW); Li-Chieh Chuang, Hsinchu (TW)

(72) Inventors: Feng-Wen Yen, Taipei (TW); Li-Chieh Chuang, Hsinchu (TW)

( * ) Notice: Subject to any disclaimer, the term of this patent is extended or adjusted under 35 U.S.C. 154(b) by 374 days.

(21) Appl. No.: 15/375,182

(22) Filed: Dec. 12, 2016

(65) Prior Publication Data
US 2018/0166640 A1 Jun. 14, 2018

(51) Int. Cl.
*H01L 51/00* (2006.01)
*C09K 11/02* (2006.01)
(Continued)

(52) U.S. Cl.
CPC ........ *H01L 51/0074* (2013.01); *C07D 495/04* (2013.01); *C09K 11/02* (2013.01); *C09K 11/06* (2013.01); *H01L 51/0067* (2013.01); *C09K 2211/1007* (2013.01); *C09K 2211/1044* (2013.01); *C09K 2211/1059* (2013.01); *C09K 2211/1092* (2013.01); *H01L 51/5016* (2013.01);
(Continued)

(58) Field of Classification Search
None
See application file for complete search history.

(56) References Cited

U.S. PATENT DOCUMENTS 7,820,782 B2 * 10/2010 Ong .................... C08G 61/126
257/40
9,112,157 B2    8/2015 Brown et al.
(Continued)

FOREIGN PATENT DOCUMENTS

CN     103664994 A  * 12/2012  ............. C09K 11/06
KR  1020130090726 A  *  8/2013  ............. C07D 471/04

*Primary Examiner* — Robert S Loewe

(57) ABSTRACT

The present invention discloses an organic compound represented by the following formula (1), the organic EL device employing the organic compound as light emitting host of emitting lay and/or an electron transporting layer, and/or a hole blocking layer, and/or a delayed fluorescence material of emitting layer can display good performance.

formula (1)

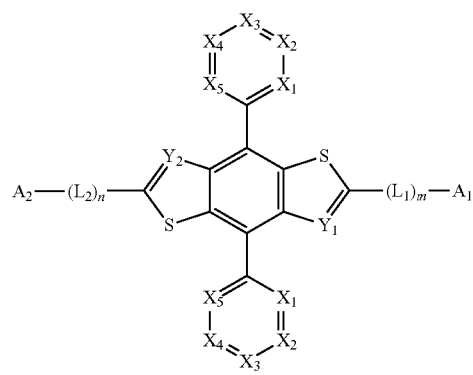

wherein $A_1$ and $A_2$ are acceptor, m, n, $L_1$, $L_2$, $Y_1$, $Y_2$ and $X_1$ to $X_5$ are the same definition as described in the present invention.

16 Claims, 1 Drawing Sheet

| 14 | — metal electrode |
| 13 | — electron injection layer |
| 12 | — electron transport layer |
| 11 | — hole blocking layer |
| 10 | — emitting layer |
| 9  | — electron blocking layer |
| 8  | — hole transport layer |
| 7  | — hole injection layer |
| 6  | — transparent electrode |

(51) Int. Cl.
*C09K 11/06* (2006.01)
*C07D 495/04* (2006.01)
*H01L 51/50* (2006.01)

(52) U.S. Cl.
CPC ...... *H01L 51/5072* (2013.01); *H01L 51/5096* (2013.01)

(56) References Cited

U.S. PATENT DOCUMENTS

| | | | | |
|---|---|---|---|---|
| 2005/0234159 A1* | 10/2005 | Takeuchi | ................ | C08K 5/01 524/90 |
| 2011/0049477 A1* | 3/2011 | Meng | ................... | C07D 493/04 257/40 |

* cited by examiner

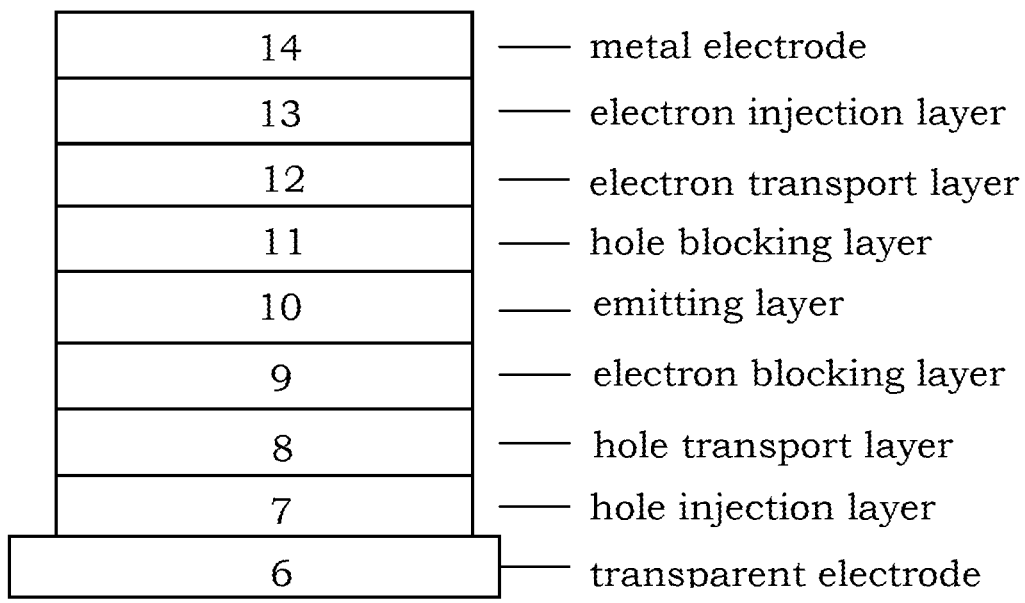

ORGANIC COMPOUND FOR ORGANIC EL DEVICE AND USING THE SAME

FIELD OF INVENTION

The present invention relates to an organic compound and organic electroluminescence (herein referred to as organic EL) device using the compound. More specifically, the present invention relates to an organic compound comprises general formula (1), and an organic EL device uses the compound as delayed fluorescence material of emitting layer and/or phosphorescent light emitting host of emitting layer, and/or an electron transporting layer, and/or a hole blocking layer can display excellent performance.

BACKGROUND OF THE INVENTION

Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

A new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent host for emitting layer are still unsatisfactory in half-lifetime, efficiency and driving voltage for industrial practice use. Besides, in order to display excellent performance of organic EL devices, the phosphorescent light emitting host material need to collocate with other organic thin film layer such as hole blocking layer and electron transporting layer to get lower power consumption, longer half-life time and higher efficiency. Therefore, there is a demand for designing and developing novel material for organic EL devices.

In the present invention, for the purpose to prolong the half-life time, higher efficiency and display excellent performance for dipolar materials of delayed fluorescence compound for organic EL device, we employ benzodithiophene core as donor and linked to some efficient acceptors such as formula (2) to formula (11) to form series of dipolar material as formula (1), those organic compounds could be used as delayed fluorescence material of emitting layer and/or phosphorescent light emitting host of emitting layer, and/or an electron transporting layer, and/or a hole blocking layer.

SUMMARY OF THE INVENTION

According to the reasons described above, the present invention has the objective of resolving such problems of the prior art and offering a light emitting device which is excellent in its thermal stability, high luminance efficiency and long half-life time. The present invention disclose an organic compound having general formula (1), used as delayed fluorescence material of emitting layer and/or phosphorescent light emitting host of emitting layer, and/or an electron transporting layer, and/or a hole blocking layer having good charge carrier mobility and excellent operational durability can lower driving voltage and power consumption, increasing efficiency and half-life time of organic EL device.

The present invention has the economic advantages for industrial practice. Accordingly, the present invention discloses the organic compound which can be used for organic EL device is disclosed. The mentioned the organic compound is represented by the following formula (1):

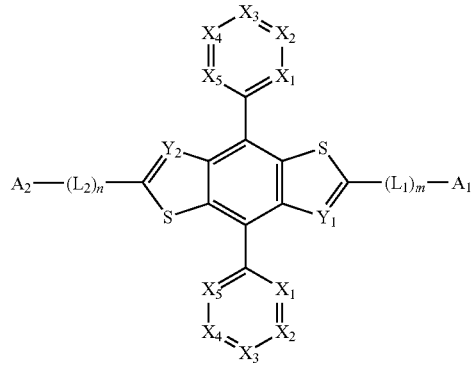

formula (1)

wherein $A_1$ and $A_2$ are acceptor represented from formula (2) to formula (11)

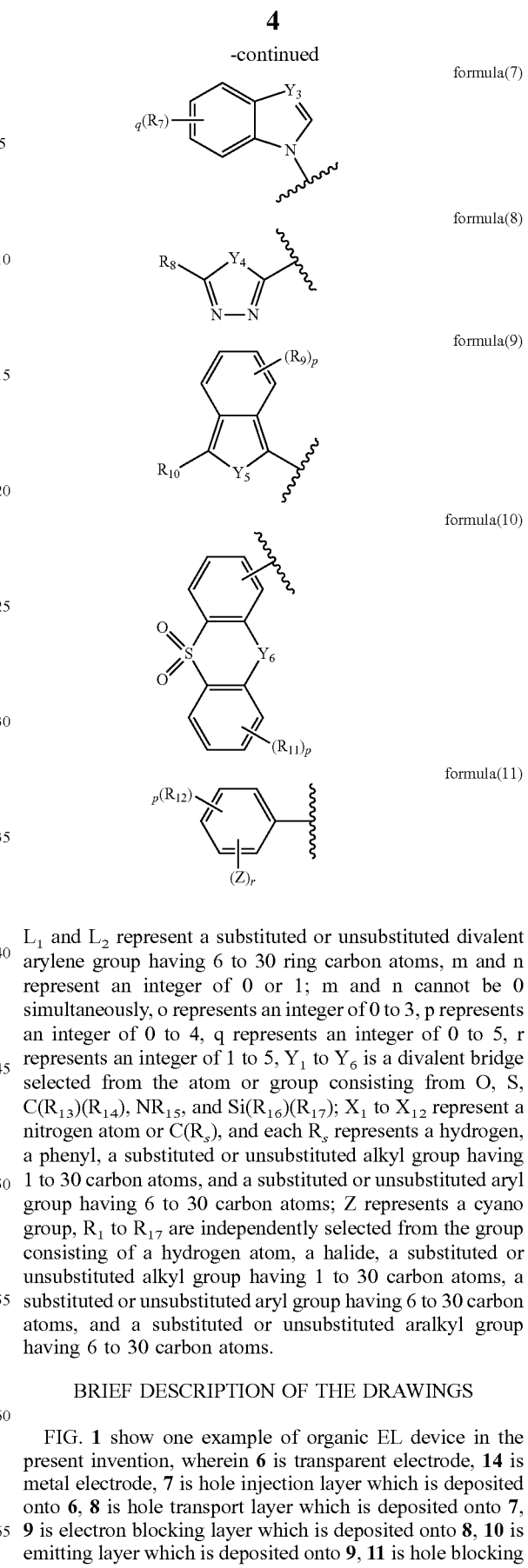

$L_1$ and $L_2$ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, $Y_1$ to $Y_6$ is a divalent bridge selected from the atom or group consisting from O, S, $C(R_{13})(R_{14})$, $NR_{15}$, and $Si(R_{16})(R_{17})$; $X_1$ to $X_{12}$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms; Z represents a cyano group, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the organic compound for organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic compound which can be used as delayed fluorescence material of emitting layer and/or phosphorescent light emitting host of emitting layer, and/or an electron transporting layer, and/or a hole blocking layer a thermally activated delayed fluorescence (TADF) material of emitting layer for organic EL device are disclosed. The mentioned the organic compound represented by the following formula (1):

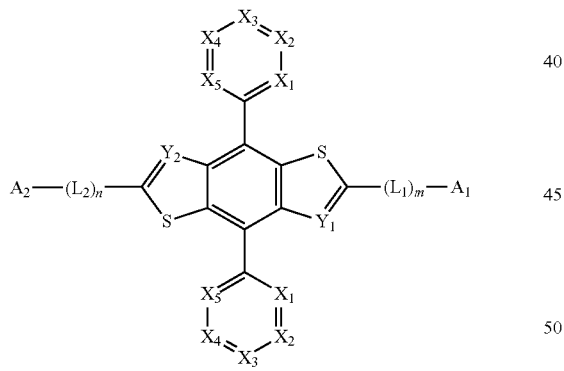

formula (1)

wherein $A_1$ and $A_2$ are acceptor represented from formula (2) to formula (11)

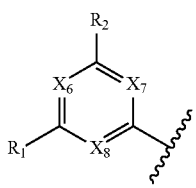

formula(2)

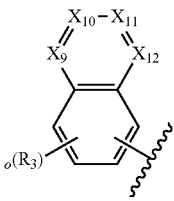

formula(3)

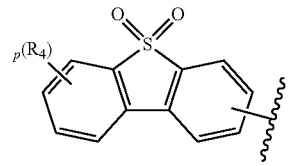

formula(4)

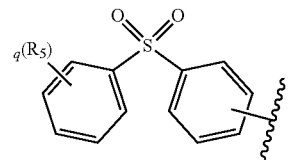

formula(5)

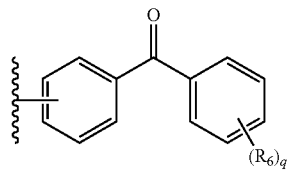

formula(6)

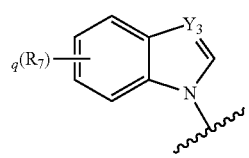

formula(7)

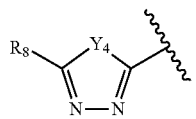

formula(8)

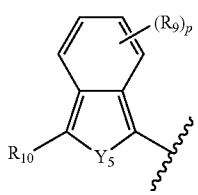

formula(9)

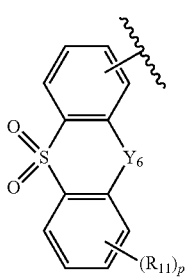

formula(10)

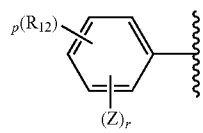

formula(11)

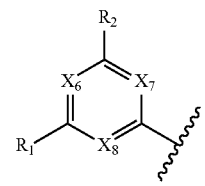

formula(2)

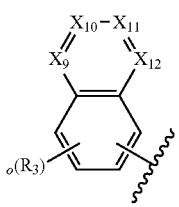

formula(3)

L₁ and L₂ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, $Y_1$ to $Y_6$ is a divalent bridge selected from the atom or group consisting from O, S, $C(R_{13})(R_{14})$, $NR_{15}$, and $Si(R_{16})(R_{17})$; $X_1$ to $X_{12}$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms; Z represents a cyano group, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

According to the above-mentioned the organic compound formula (1), wherein the organic compound formula (1) is represented by the following formula (12) or formula (13):

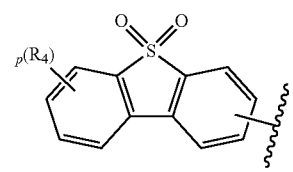

formula(4)

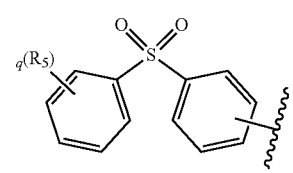

formula(5)

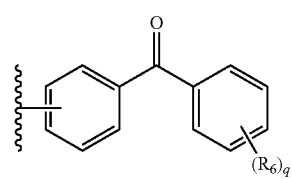

formula(6)

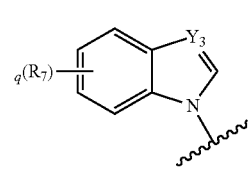

formula(7)

formula (12)

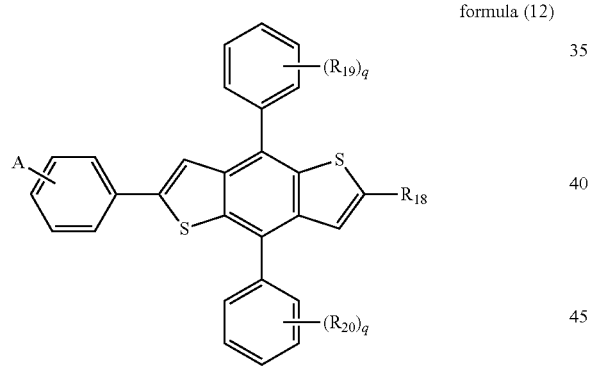

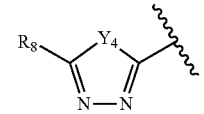

formula(8)

formula (13)

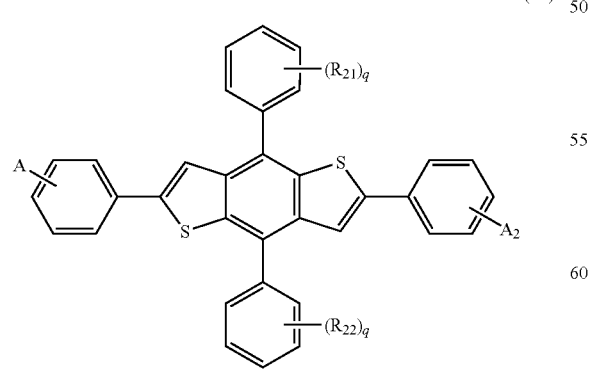

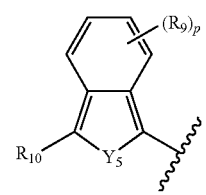

formula(9)

wherein $A_1$ and $A_2$ are acceptor represented from formula (2) to formula (11)

-continued formula(10)

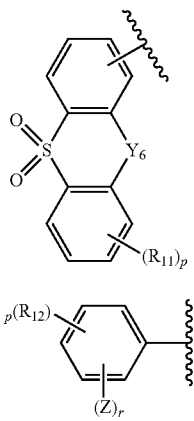

formula(11)

$L_1$ and $L_2$ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, Z is represents a cyano group, $R_1$ to $R_{12}$ and $R_{19}$ to $R_{22}$) are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

In this embodiment, some organic compounds are shown below:

Compound 1

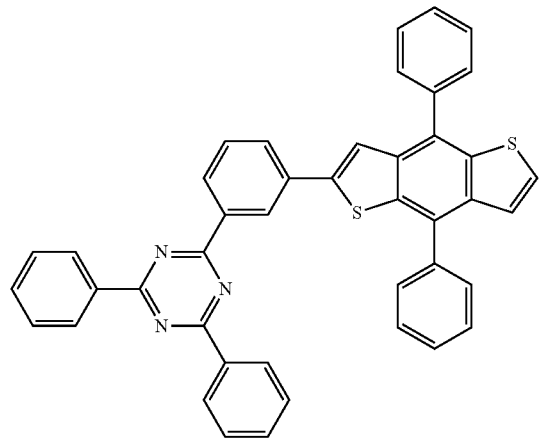

Compound 2

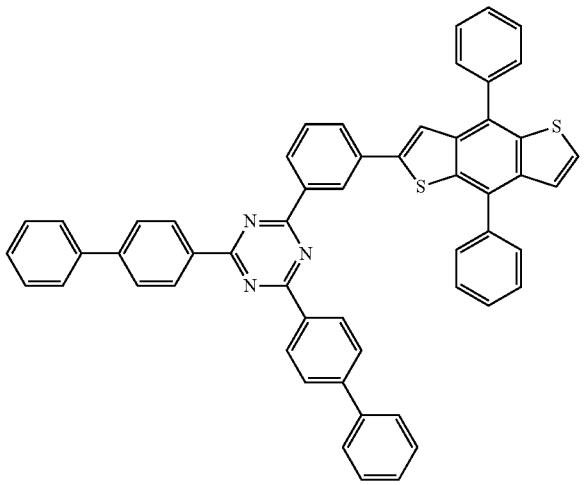

Compound 3

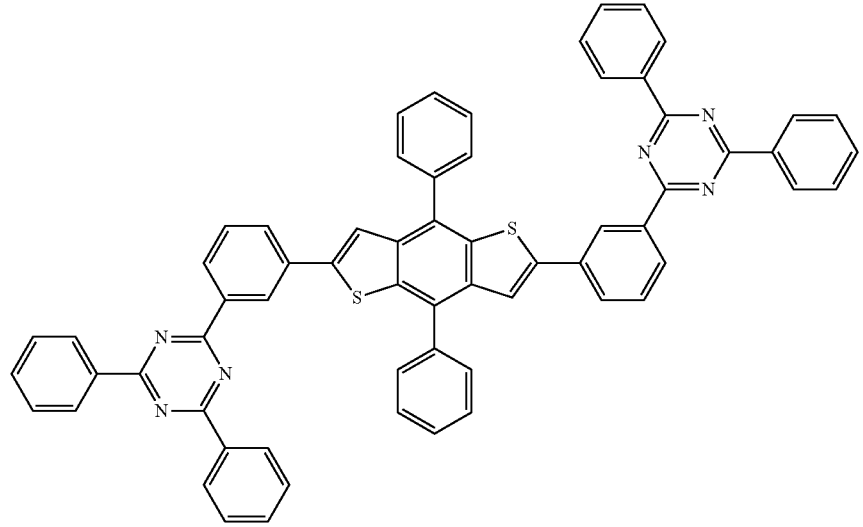

-continued
Compound 4
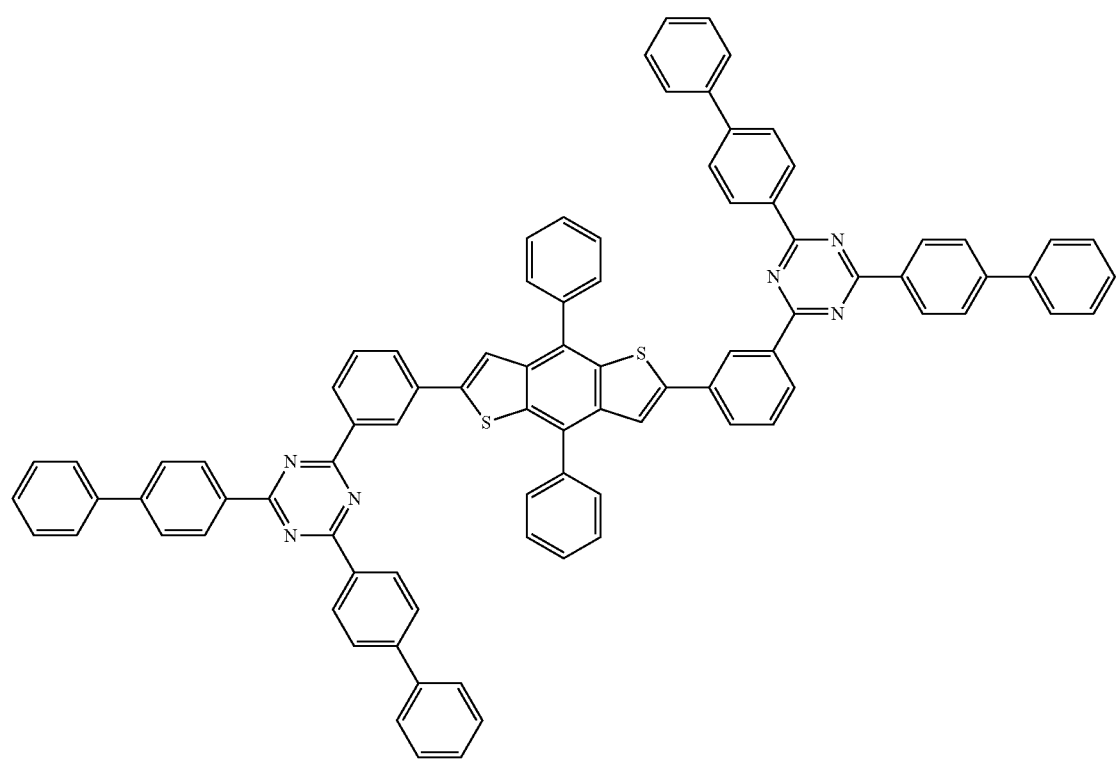
Compound 5
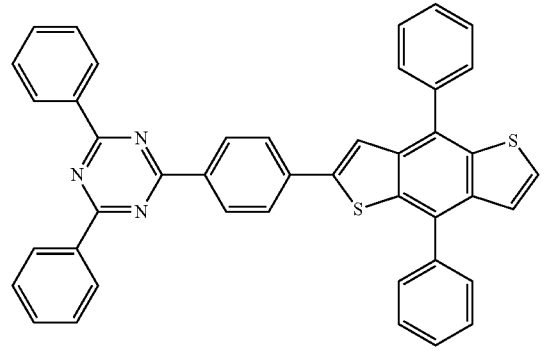
Compound 6
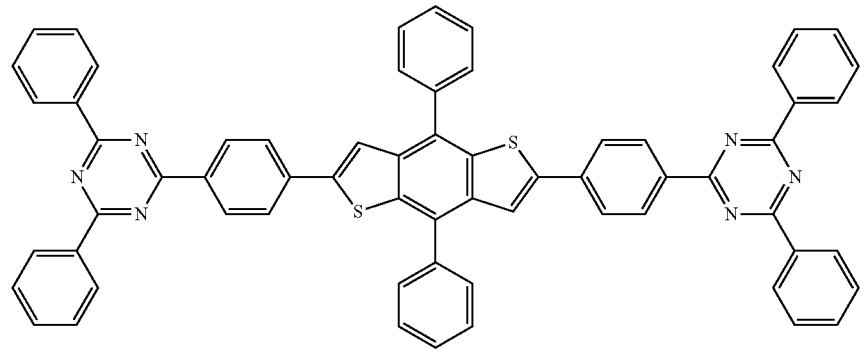

-continued
Compound 7
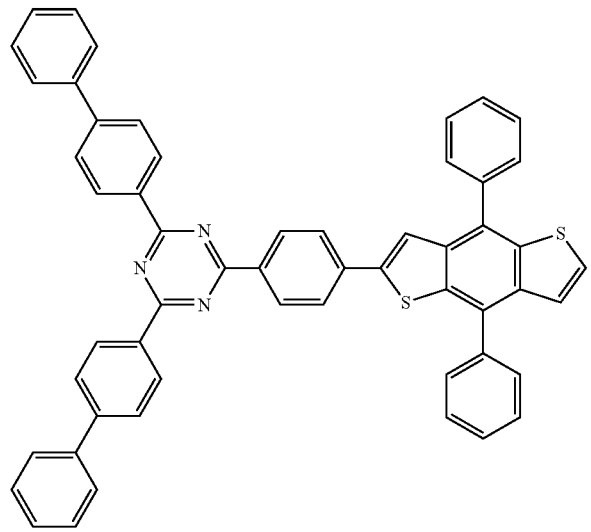
Compound 8
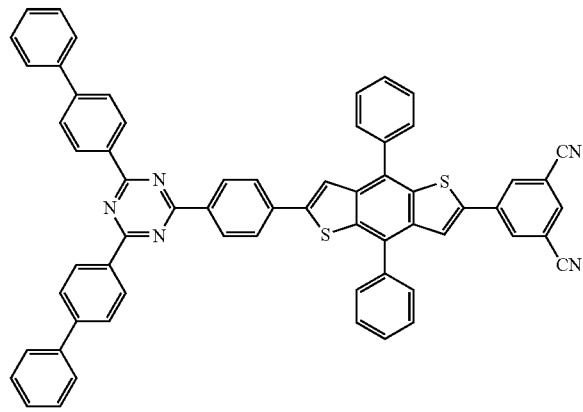
Compound 9
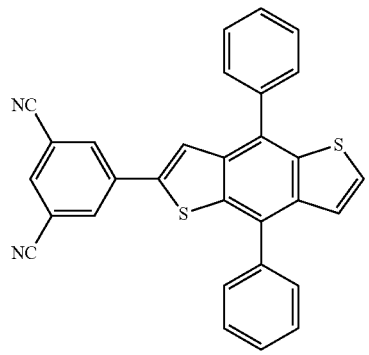
Compound 10
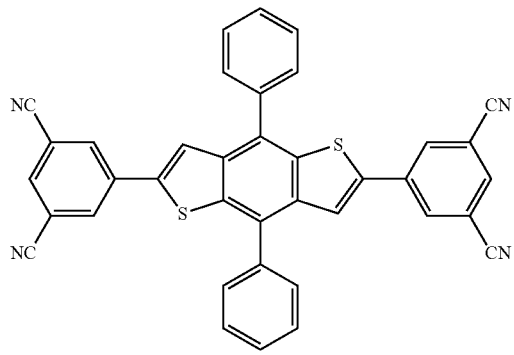
Compound 11
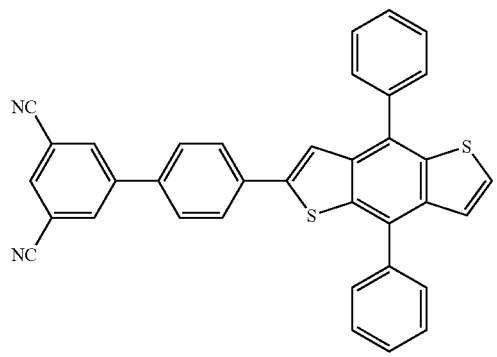
Compound 12
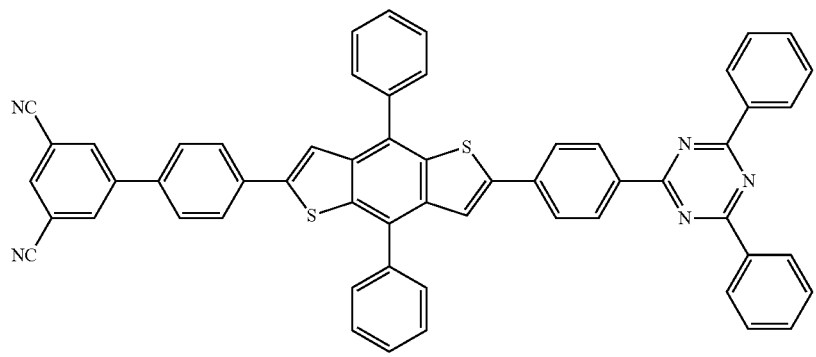

-continued
Compound 13
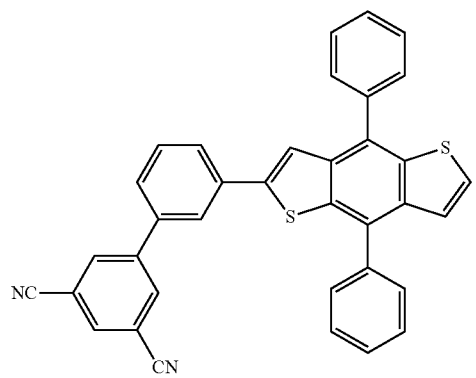
Compound 14
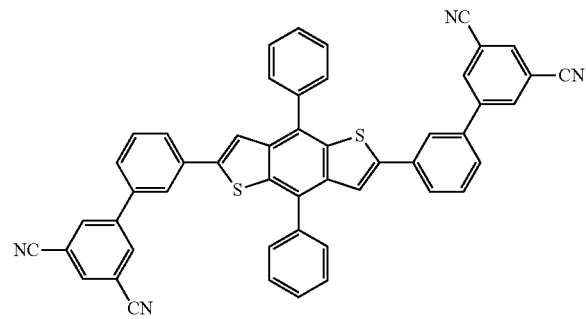
Compound 15
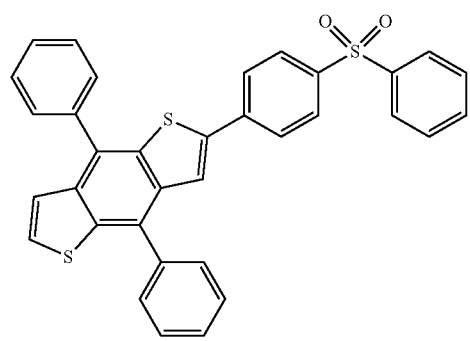
Compound 16
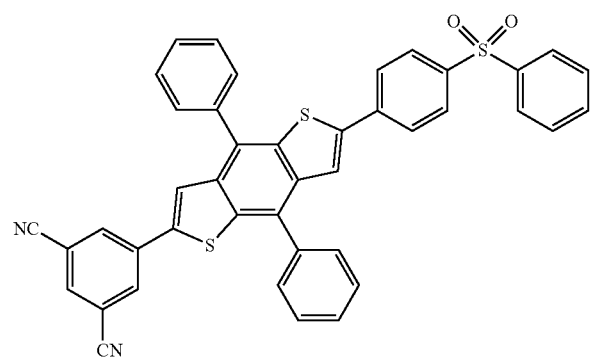
Compound 17
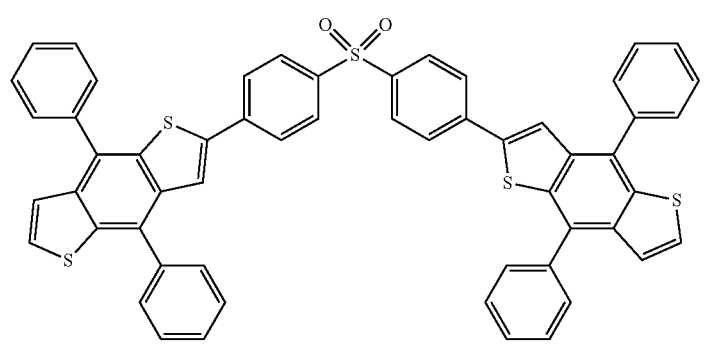
Compound 18
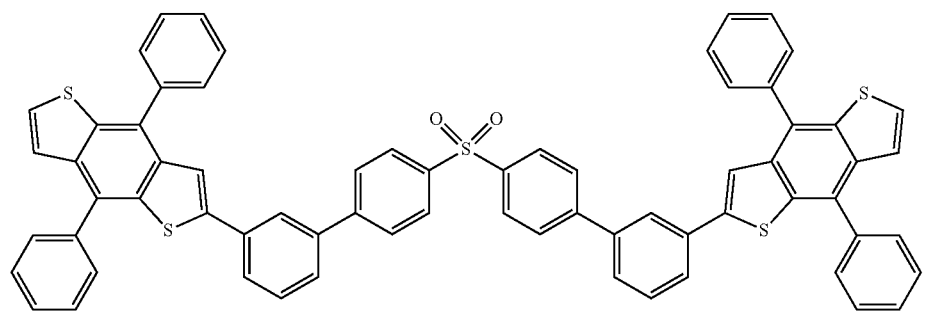

-continued
Compound 19
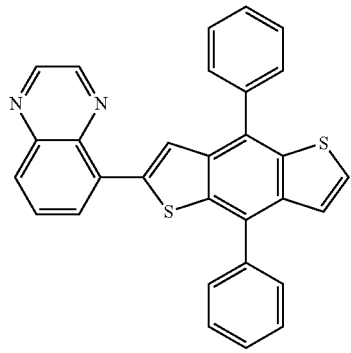
Compound 20
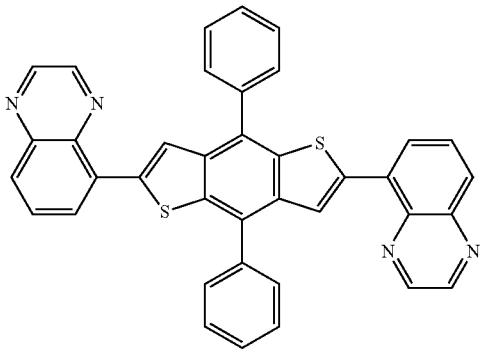
Compound 21
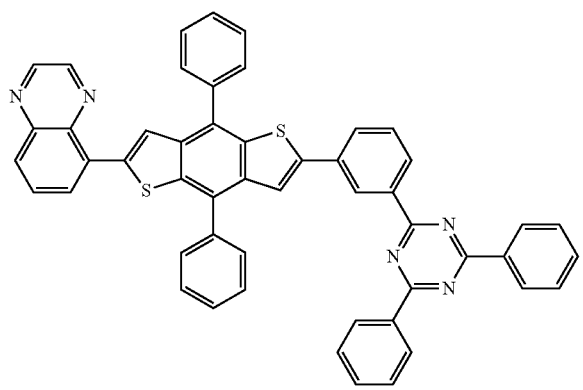
Compound 22
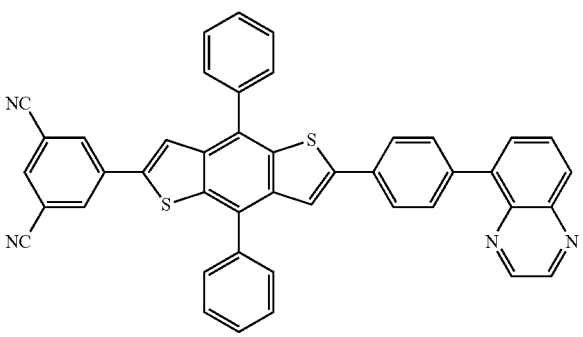
Compound 23
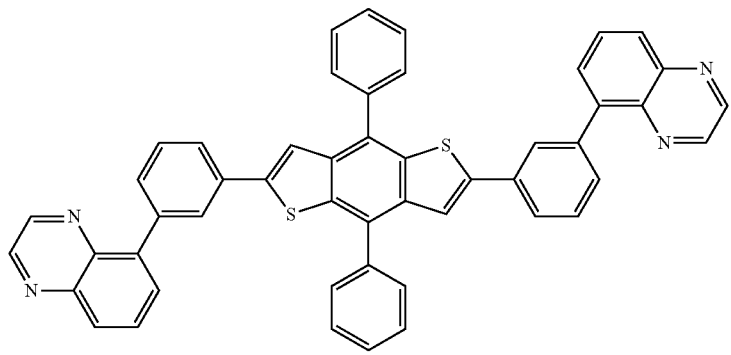
Compound 24
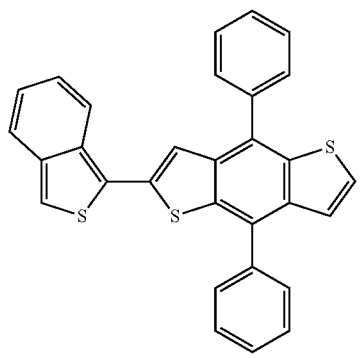
Compound 25
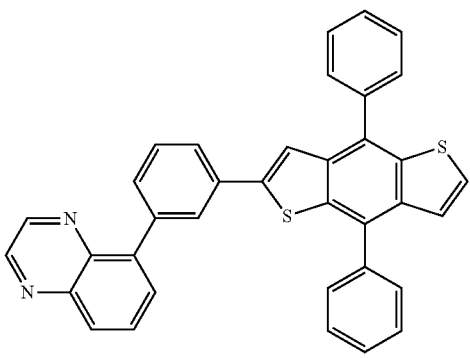

-continued
Compound 26
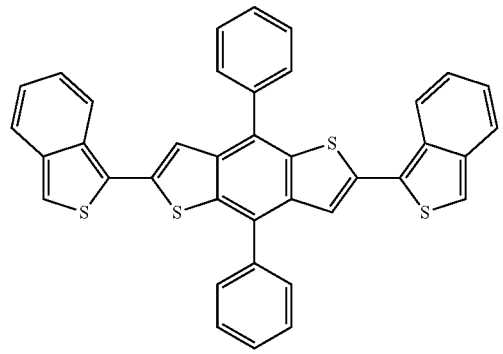
Compound 27
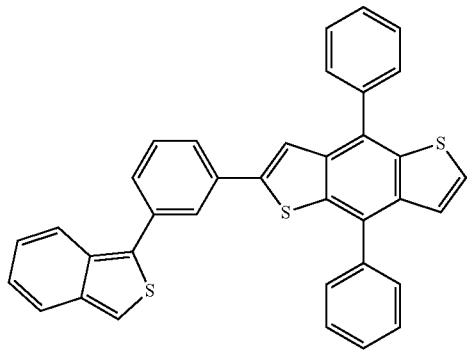
Compound 28
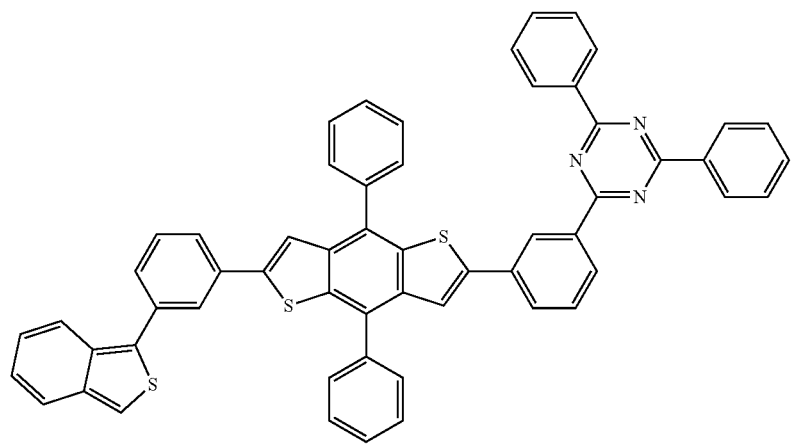
Compound 29
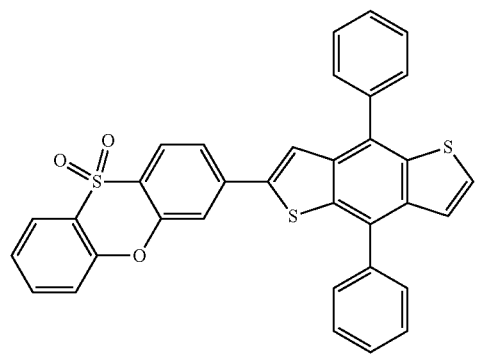
Compound 30
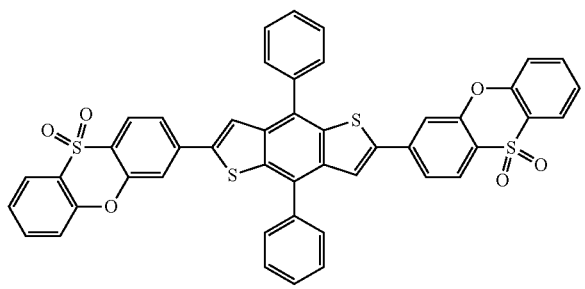

Compound 31
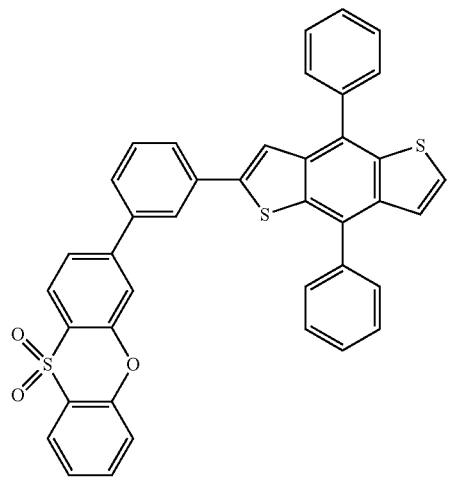
Compound 32
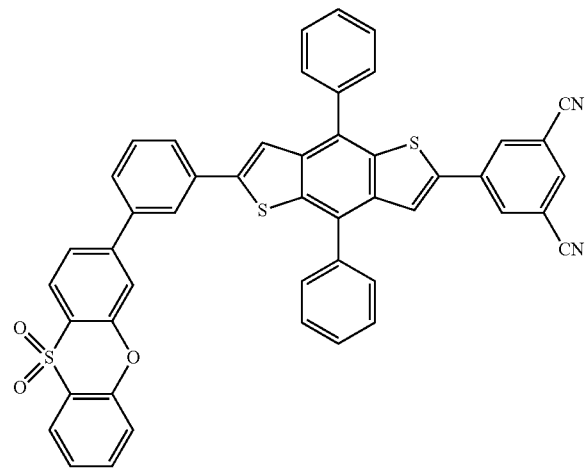
Compound 33
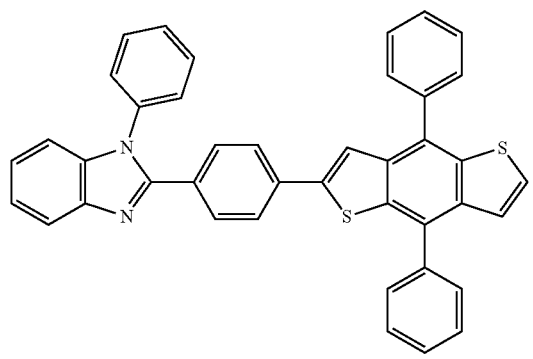
Compound 34
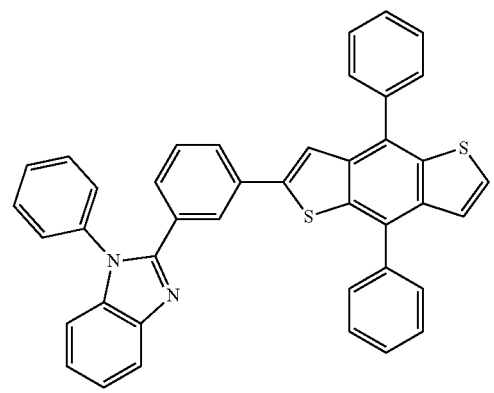
Compound 35
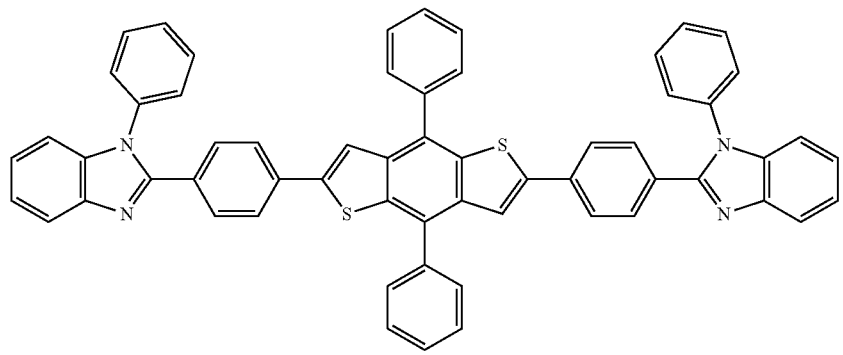

Compound 36
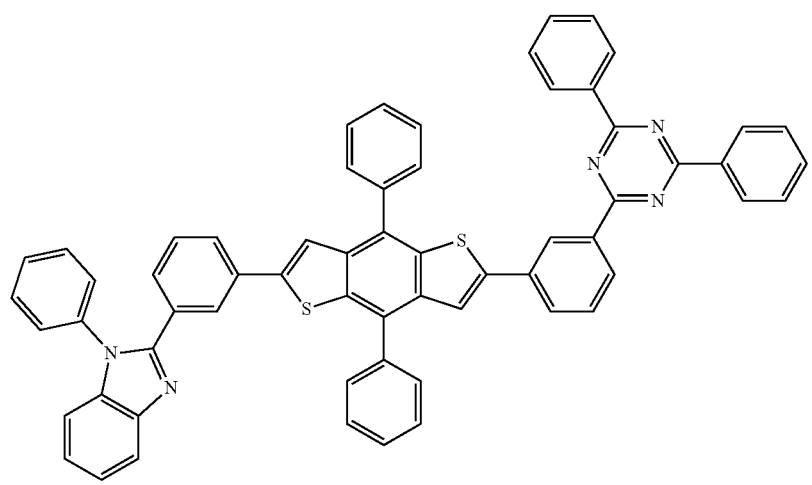
Compound 37
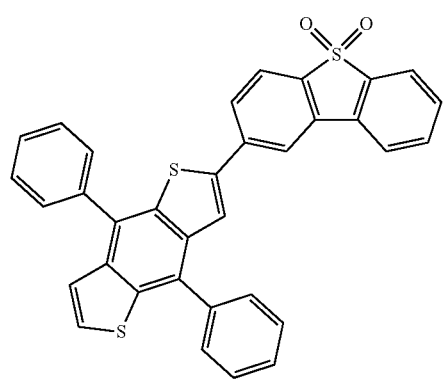
Compound 38
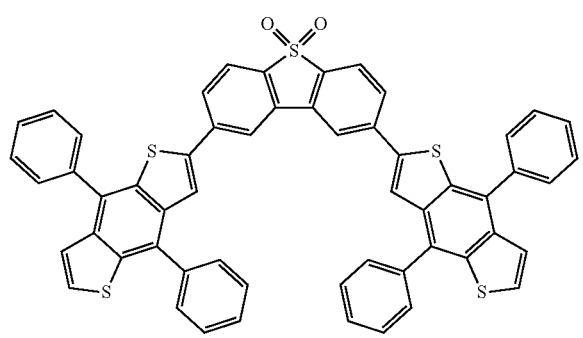
Compound 39
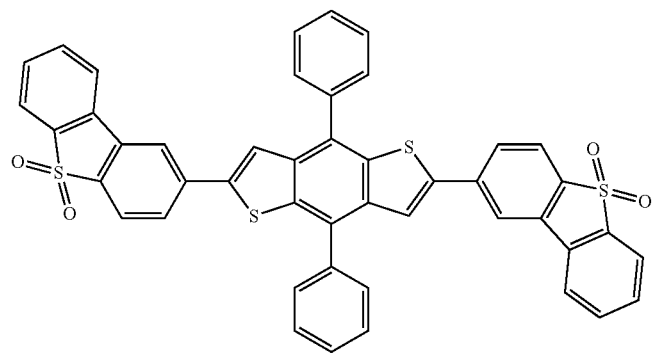

Compound 40
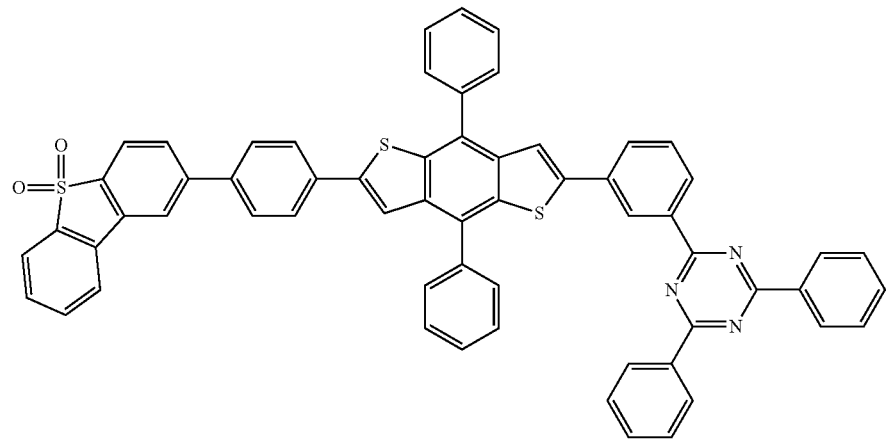
Compound 41
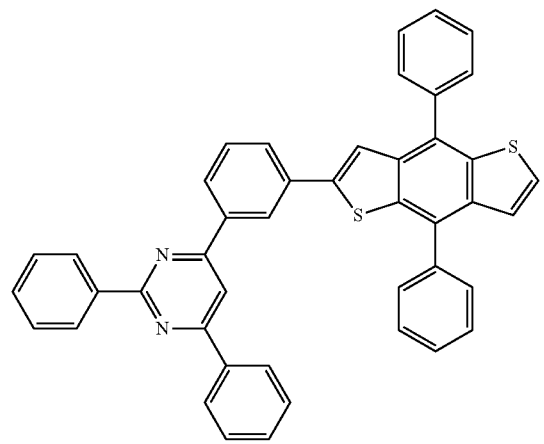
Compound 42
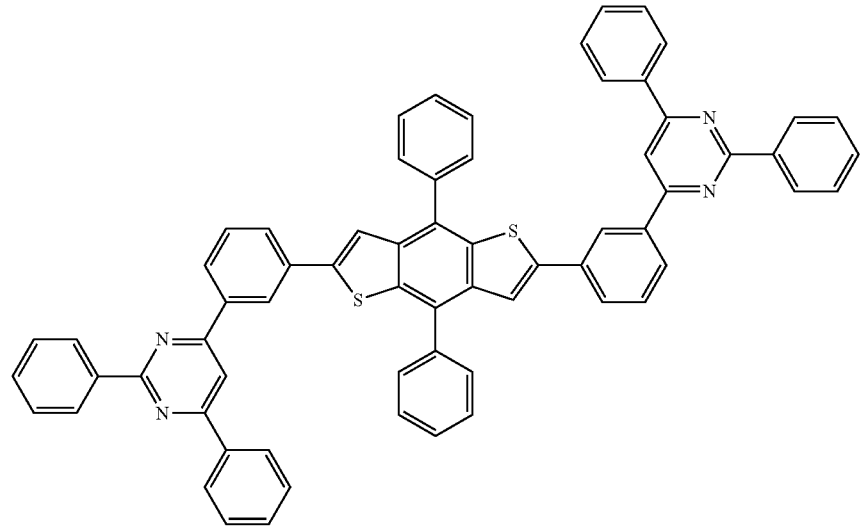

-continued
Compound 43
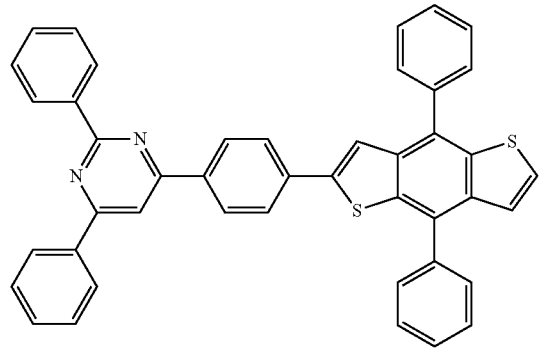
Compound 44
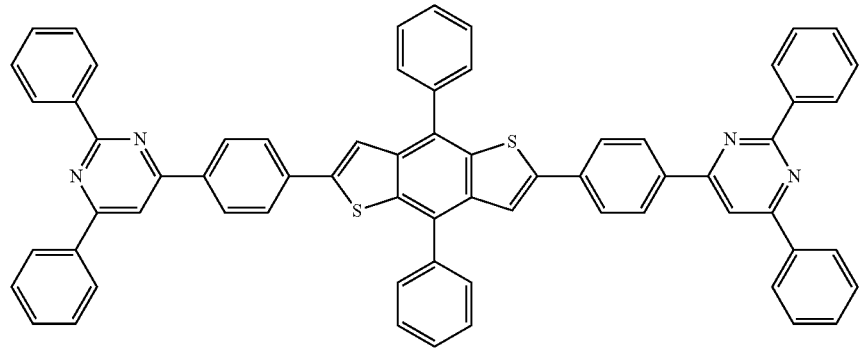
Compound 45
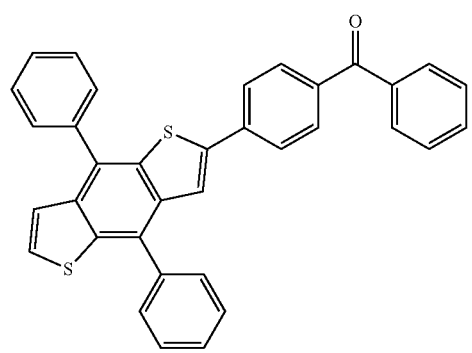
Compound 46
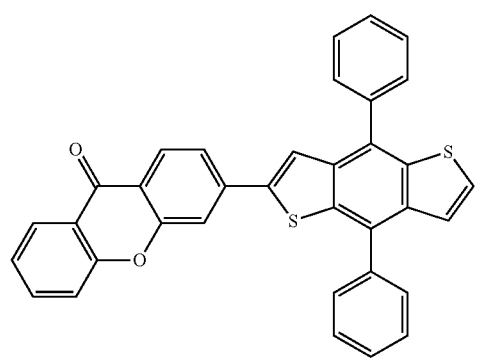
Compound 47
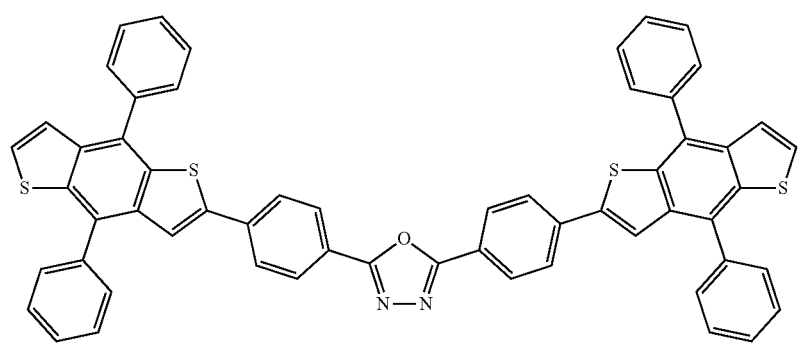

Compound 48

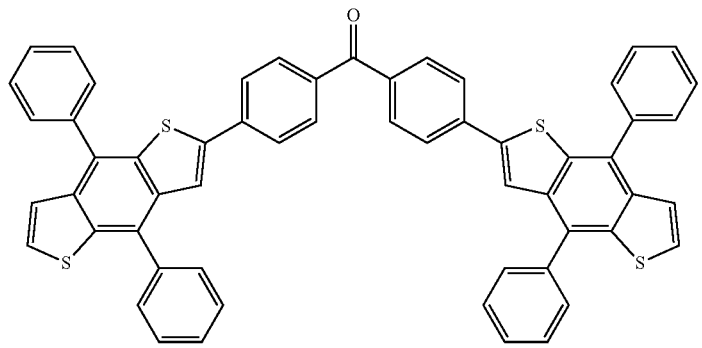

Compound 49

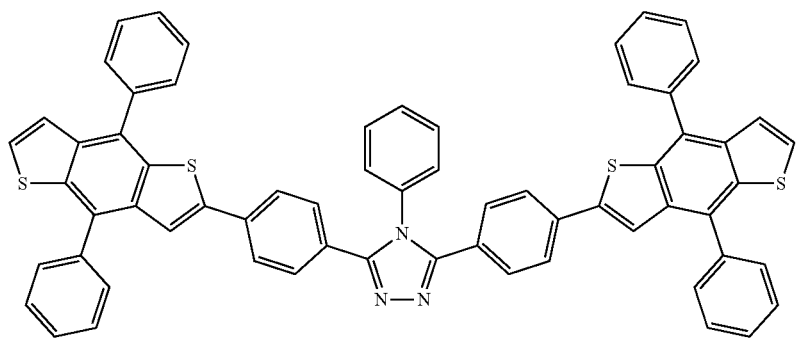

Compound 50

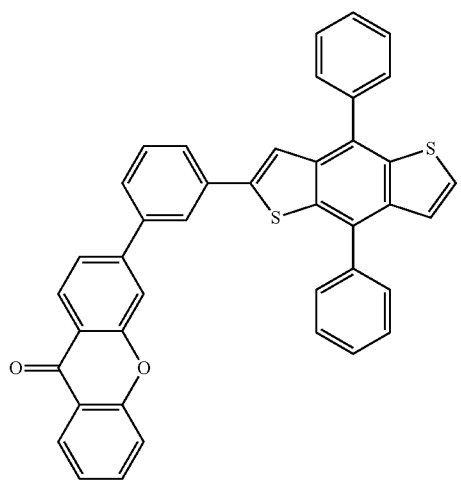

Detailed preparation for the organic compound in the present invention could be clarified by exemplary embodiments, but the present invention is not limited to exemplary embodiments. EXAMPLE 1 to EXAMPLE 5 show the preparation for examples of the organic compound in the present invention. EXAMPLE 6 show the fabrication of organic EL device and I-V-B, half-life time of organic EL device testing report.

EXAMPLE 1

Synthesis of Compound 1

Synthesis of 4,8-diphenylbenzo[1,2-b:4,5-b']dithiophene

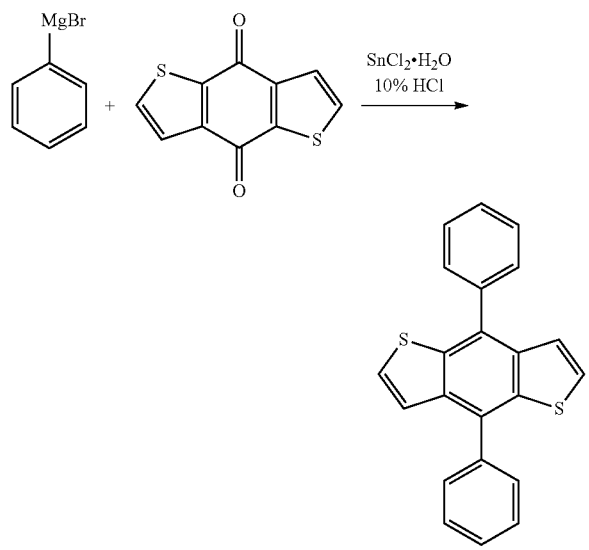

A mixture of 5 g (22.7 mmol) of 4,8-dihydrobenzo[1,2-b:4,5-b'] dithiophene-4,8-dione and 400 mL of THF was cooled in an ice bath and the 90.8 mL of phenylmagnesium bromide (1M in THF, 90.8 mmol) was dropwise into then reflux for 1 h. The resulting mixture was allowed to cool to room temperature, and the solution of tin chloride (70 g in 120 mL 10% HCl, 0.34 mole) was dropwise into then reflux for 2 h. The resulting mixture was allowed to cool to room temperature and the solution was removed. The 200 mL of methanol was added, then filtered to get the brown solid, yield (6 g, 77.2%). 1H NMR (CDCl3, 400 MHz): chemical shift (ppm) 7.76-7.78 (dd, 4H), 7.40-7.52 (m, 10H).

Synthesis of 2-bromo-4,8-diphenylbenzo[1,2-b:4,5-b']dithiophene

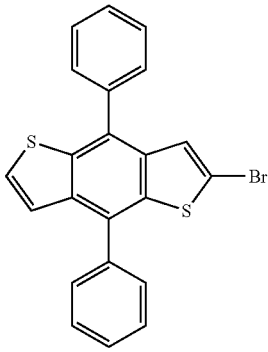

A mixture of 2 g (5.84 mmol) of 4,8-diphenylbenzo[1,2-b:4,5-b'] dithiophene and 300 mL of THF was cooled in a dry ice bath and the 3.5 mL of n-butyllithium (2.5M in Hexane, 8.76 mmol) was dropwise into then stir for 1 h in a dry ice bath. The resulting mixture was stirred for 1 h at the room temperature then the resulting mixture was cooled in a dry ice bath and the 1.4 mL of 1,2-dibromotetrachloroethane (11.68 mmol) was dropwise into then stir for 1 h in a dry ice bath then the resulting mixture was stirred at the room temperature for 12 h. The 50 mL of water was added, then removed the solution. The 50 mL of methanol was added, then filtered to get the white solid, yield (1.8 g, 75%). 1H NMR (CDCl3, 400 MHz): chemical shift (ppm) 7.76-7.78 (dd, 2H), 7.40-7.51 (m, 10H), 7.23 (s, 1H).

Synthesis of Compound 1

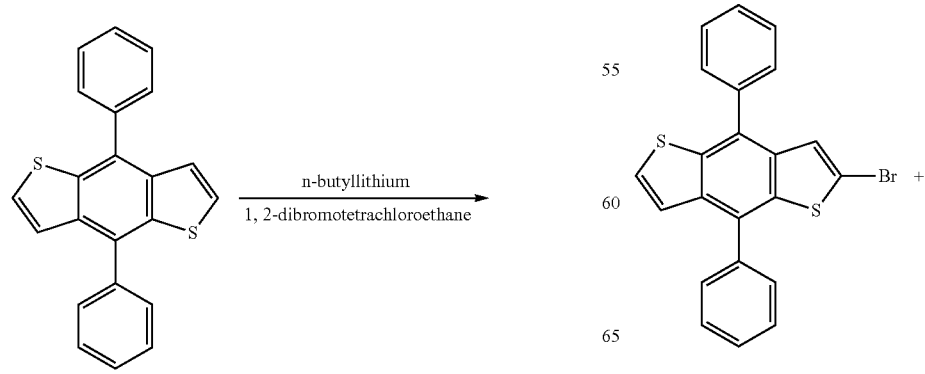

EXAMPLE 2

Synthesis of Compound 3

Synthesis of 2,6-dibromo-4,8-diphenylbenzo[1,2-b:4,5-b']dithiophene

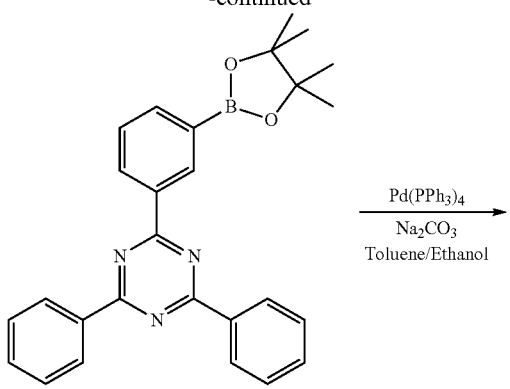

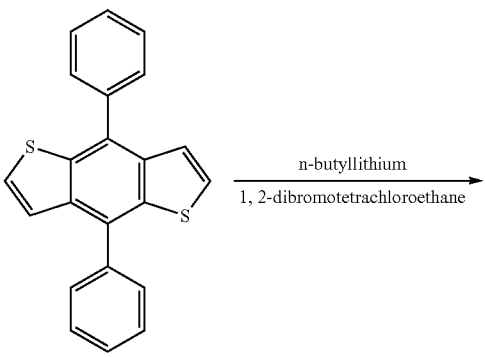

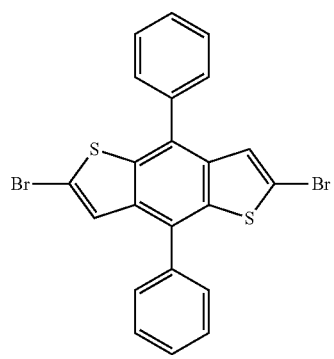

A mixture of 1.8 g (4.27 mmol) of 2-bromo-4,8-diphenylbenzo[1,2-b:4,5-b']dithiophene and 2.23 g (5.13 mmol) of 2,4-diphenyl-6-(3-(4,4,5,5-tetra methyl-1,3,2-dioxaborolan-2-yl)phenyl)-1,3,5-triazine, 0.1 g (0.08 mmol) of Pd(PPh$_3$)$_4$, 8 ml of 2M Na$_2$CO$_{3(aq)}$, 50 ml of EtOH and 150 ml toluene was degassed and placed under nitrogen, and then heated at 100° C. for 12 h. After finishing the reaction, the mixture was allowed to cool to room temperature. The 250 mL of methanol was added, then filtered and washed by methanol to get the yellow solid, yield (1.3 g, 46%). 1H NMR (CDCl3, 400 MHz): chemical shift (ppm) 9.04 (s, 1H), 8.74 (d, 4H), 8.67 (d, 1H), 7.84 (d, 1H), 7.76-7.82 (m, 4H), 7.72 (s, 1H), 7.50-7.66 (m, 13H), 7.40 (d, 1H), 7.32 (d, 1H). MS (m/z, EI$^+$): 649.5

A mixture of 2 g (5.84 mmol) of 4,8-diphenylbenzo[1,2-b:4,5-b'] dithiophene and 300 mL of THF was cooled in a dry ice bath and the 7 mL of n-butyllithium (2.5M in Hexane, 17.52 mmol) was dropwise into then stir for 1 h in a dry ice bath. The resulting mixture was stirred for 1 h at the room temperature then the resulting mixture was cooled in a dry ice bath and the 2.8 mL of 1,2-dibromotetrachloroethane (23.36 mmol) was dropwise into then stir for 1 h in a dry ice bath then the resulting mixture was stirred at the room temperature for 12 h. The 50 mL of water was added, then removed the solution. The 50 mL of methanol was added, then filtered to get the white solid, yield (2.3 g, 79%). 1H NMR (CDCl3, 400 MHz): chemical shift (ppm) 7.42-7.53 (m, 10H), 7.24 (s, 2H).

Synthesis of Compound 3

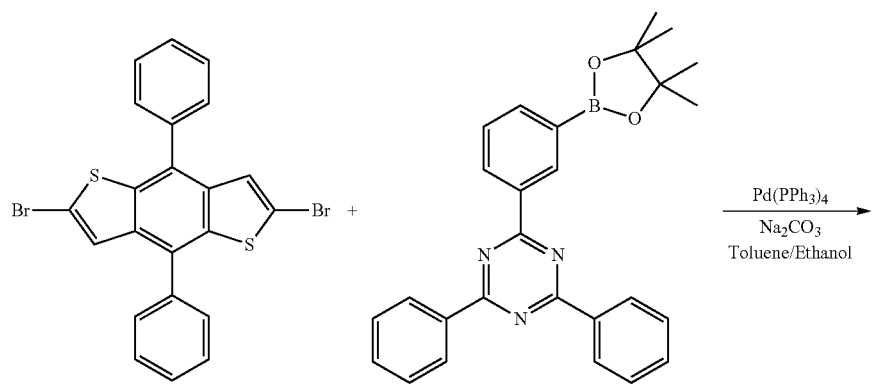

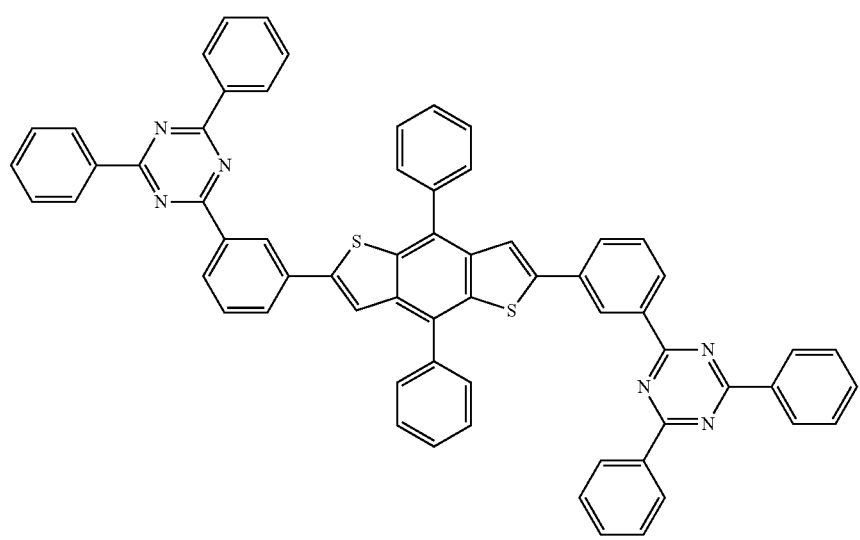

A mixture of 2 g (4 mmol) of 2,6-dibromo-4,8-diphenyl-benzo[1,2-b: 4,5-b']dithiophene and 3.83 g (8.8 mmol) of 2,4-diphenyl-6-(3-(4,4,5,5-tetramethyl-1,3,2-dioxaborolan-2-yl)phenyl)-1,3,5-triazine, 0.1 g (0.08 mmol) of Pd(PPh$_3$)$_4$, 8 ml of 2M Na$_2$CO$_{3(aq)}$, 50 ml of EtOH and 150 ml toluene was degassed and placed under nitrogen, and then heated at 100° C. for 12 h. After finishing the reaction, the mixture was allowed to cool to room temperature, then filtered and washed by methanol to get the yellow solid, yield (2.3 g, 60%). MS (m/z, EI$^+$): 957.3

EXAMPLE 3

Synthesis of Compound 9

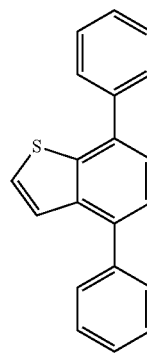

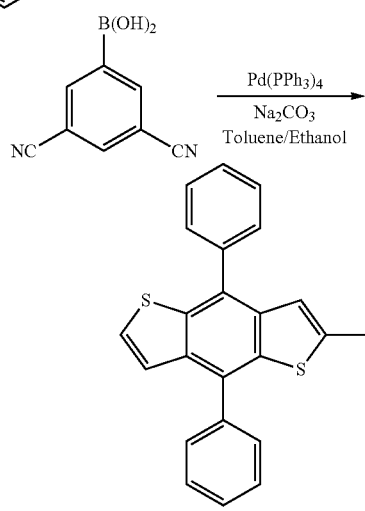

3,5-Dicyanophenylboronic acid instead of 2,4-diphenyl-6-(3-(4,4,5,5-tetramethyl-1,3,2-dioxaborolan-2-yl)phenyl)-1,3,5-triazine, except for using the same method as in synthesis Example 1, the desired compound of 2-(3,5-dicyanobenzyl)-4,8-diphenylbenzo[1,2-b:4,5-b]dithiophene was obtained. MS (m/z, EI⁺): 468.8

EXAMPLE 4

Synthesis of Compound 10

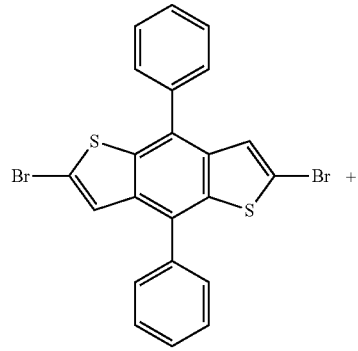

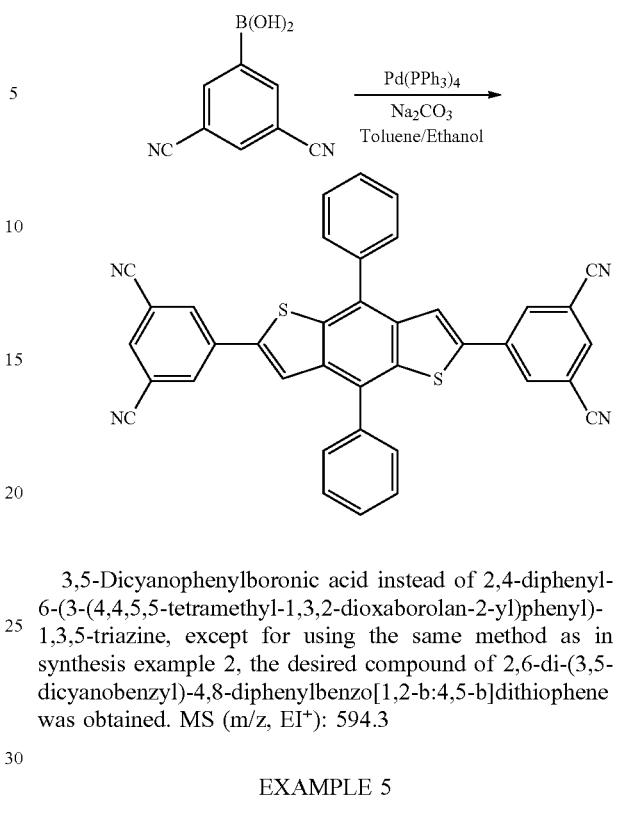

3,5-Dicyanophenylboronic acid instead of 2,4-diphenyl-6-(3-(4,4,5,5-tetramethyl-1,3,2-dioxaborolan-2-yl)phenyl)-1,3,5-triazine, except for using the same method as in synthesis example 2, the desired compound of 2,6-di-(3,5-dicyanobenzyl)-4,8-diphenylbenzo[1,2-b:4,5-b]dithiophene was obtained. MS (m/z, EI⁺): 594.3

EXAMPLE 5

Synthesis of Compound 41

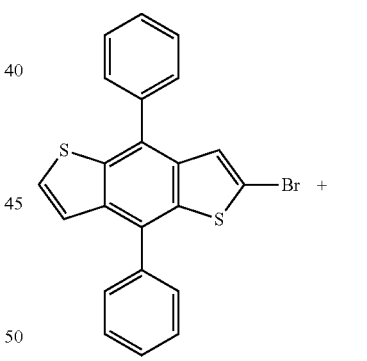

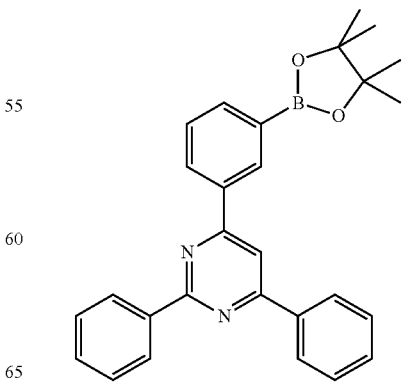

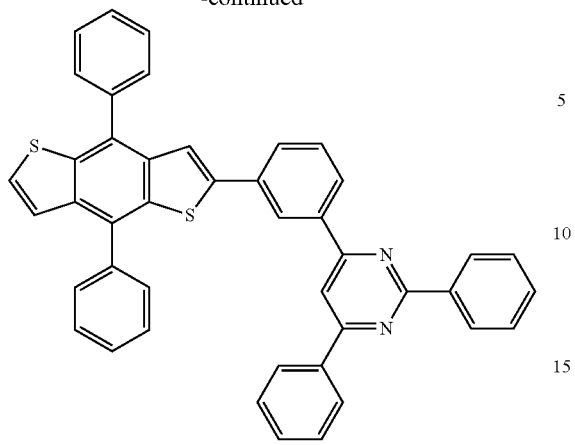

2,4-diphenyl-6-(3-(4,4,5,5-tetramethyl-1,3,2-dioxaborolan-2-yl) phenyl)pyrimidine instead of 2,4-diphenyl-6-(3-(4,4,5,5-tetramethyl-1,3,2-dioxaborolan-2-yl)phenyl)-1,3,5-triazine, except for using the same method as in synthesis Example 1, the desired compound of 2-(3-(2,6-diphenylpyrimidin-4-yl)phenyl)-4,8-diphenylbenzo[1,2-b:4,5-b']dithiophene was obtained. MS (m/z, EI$^+$): 648.5

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer, H1 used as phosphorescent host and delayed fluorescence host for comparable or standard with the present invention. The chemical structure shown below:

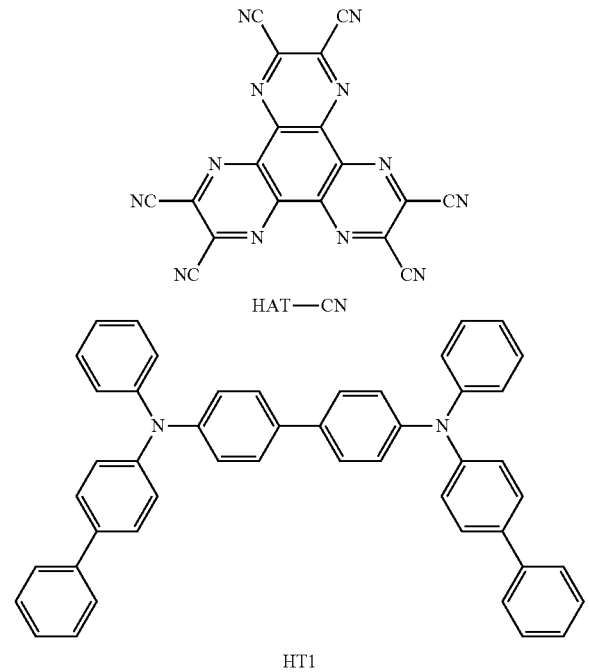

HAT—CN

HT1

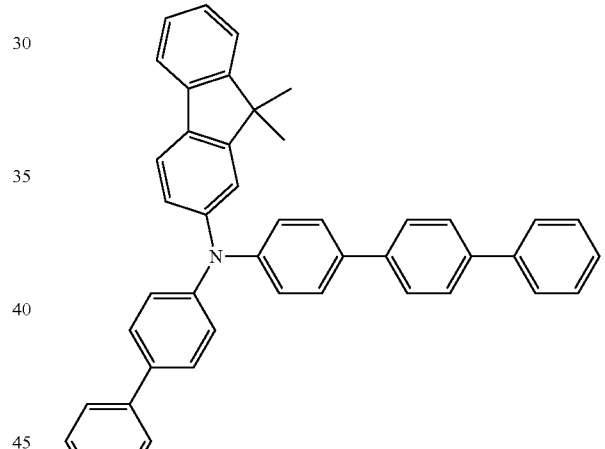

EB2

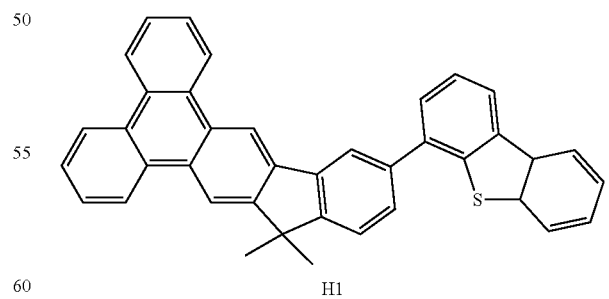

H1

The following organic compound Examples prepared in the present invention can be verified and used as delayed fluorescence dopant, phosphorescence host, hole blocking material or electron transporting material by organic EL device.

Compound 1
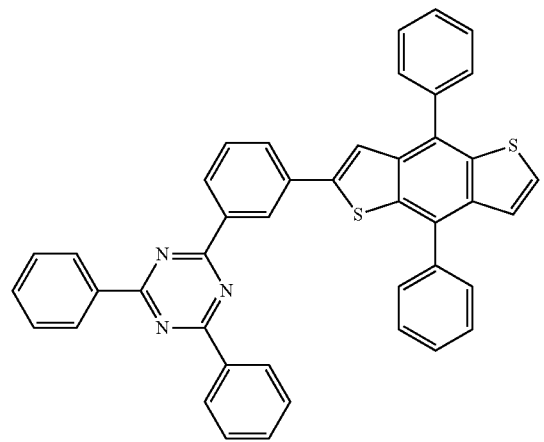
Compound 3
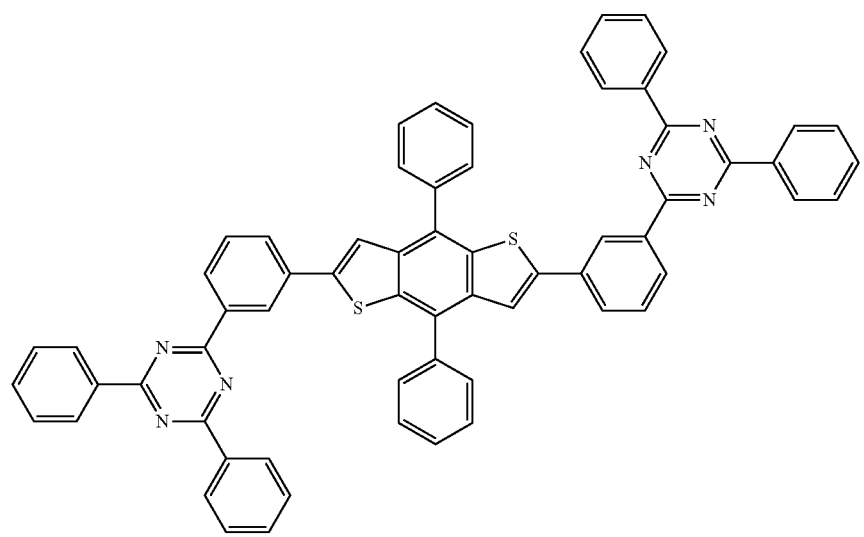
Compound 9
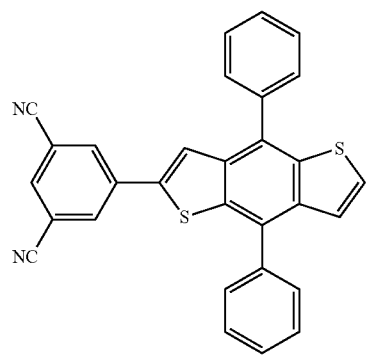
Compound 10
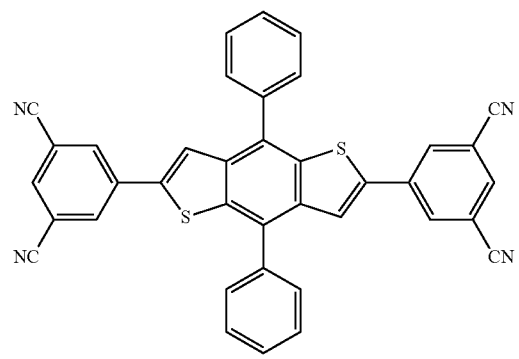

Compound 41

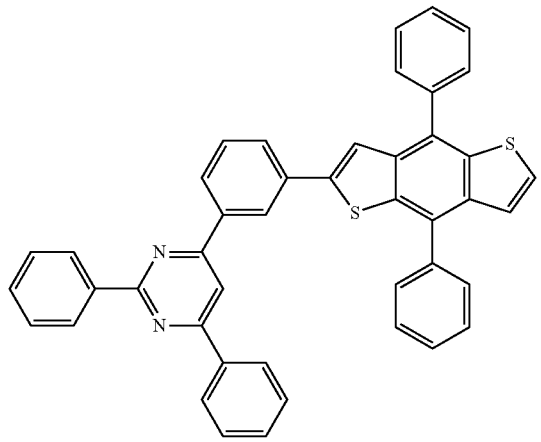

Organic iridium complexes are widely used as phosphorescent dopant for light emitting layer, Ir(ppy)$_3$ are widely used for phosphorescent green dopant of light emitting layer for organic EL device.

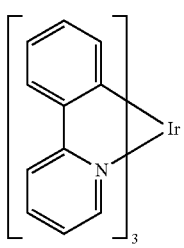

Ir(ppy)$_3$ 2,2',2''-(1,3,5-Benzinetriyl)-tris(1-phenyl-1-H-benzimidazole) (TPBi) and HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

TPBi

ET2

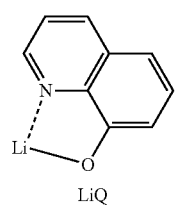

LiQ

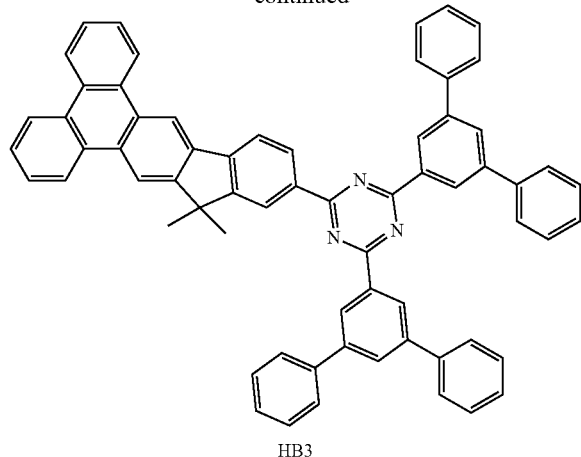

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 6

Using a procedure analogous to the above mentioned general method, organic EL device having the following device structure was produced (See FIG. 1). Device: ITO/HAT-CN (20 nm)/HT1 (110 nm)/EB2 (5 nm)/Host+dopant (30 nm)/HBM (10 nm)/ETM doped 40% LiQ (35 nm)/LiQ (1 nm)/Al (160 nm). The I-V-B (at 1000 nits) of organic EL device testing report as Table 1.

TABLE 1

| Dopant (%) | Host | HBM | ETM | Voltage (V) | Efficiency (cd/A) |
|---|---|---|---|---|---|
| C9(35%) | H1 | TPBi | ET2 | 4.2 | 25 |
| C10(35%) | H1 | TPBi | ET2 | 3.8 | 22 |
| C10(35%) | H1 | HB3 | ET2 | 3.5 | 19 |
| C1(35%) | H1 | HB3 | ET2 | 5.5 | 8 |
| C3(35%) | H1 | HB3 | ET2 | 5.8 | 11 |
| Ir(ppy)$_3$(8%) | C41 | HB3 | ET2 | 5.3 | 23 |
| Ir(ppy)$_3$(8%) | H1 | C3 | ET2 | 5.5 | 28 |
| Ir(ppy)$_3$(8%) | H1 | HB3 | C1 | 4.0 | 33 |
| Ir(ppy)$_3$(8%) | H1 | HB3 | C3 | 4.0 | 35 |
| Ir(ppy)$_3$(8%) | H1 | HB3 | ET2 | 3.5 | 32 |

In the above preferred embodiments for organic EL device testing report (see Table 1), we show that the organic compound with a general formula (1) used as light emitting host of emitting layer, and/or an electron transporting layer, and/or a hole blocking layer, and/or a delayed fluorescence (TADF) material of emitting layer for organic EL device in the present invention display good performance.

To sum up, the present invention discloses an organic compound which can be used as phosphorescent light emitting host of emitting layer, and/or an electron transporting layer, and/or a hole blocking layer, and/or a delayed fluorescence material of emitting layer for organic EL device The mentioned the organic compound represented by the following formula (1)

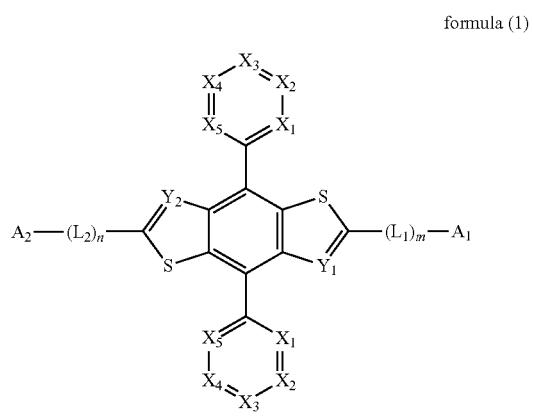

formula (1)

wherein A$_1$ and A$_2$ are acceptor represented from formula (2) to formula (11)

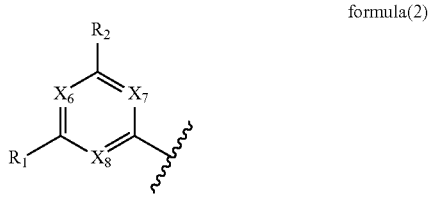

formula(2)

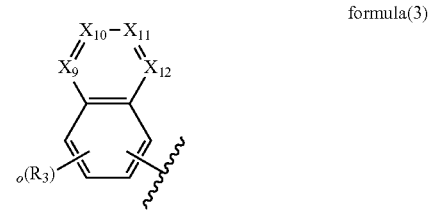

formula(3)

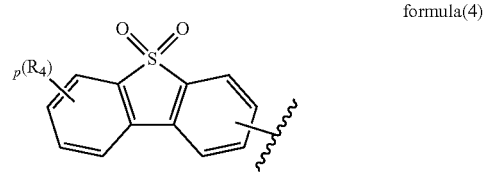

formula(4)

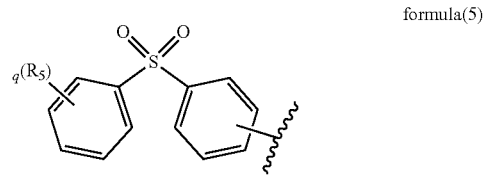

formula(5)

-continued formula(6)
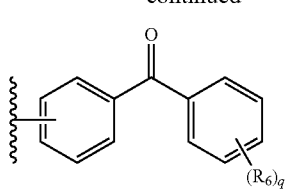

formula(7)
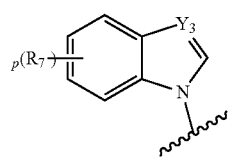

formula(8)
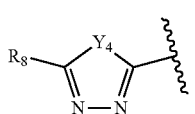

formula(9)
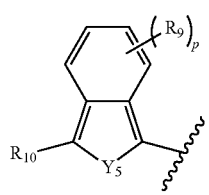

formula(10)
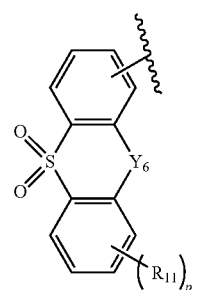

formula(11)
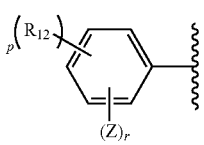

$L_1$ and $L_2$ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, $Y_1$ to $Y_6$ is a divalent bridge selected from the atom or group consisting from O, S, $C(R_{13})(R_{14})$, $NR_{15}$, and $Si(R_{16})(R_{17})$; $X_1$ to $X_{12}$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms; Z represents a cyano group, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An organic compound with a general formula (1) as follows:

formula (1)
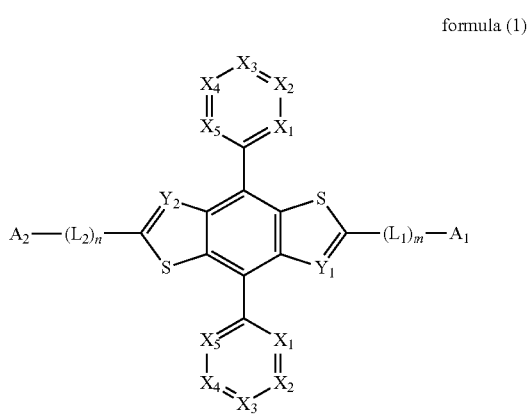

wherein $A_1$ and $A_2$ are acceptors each represented from formula (3) to formula (11)

formula(3)
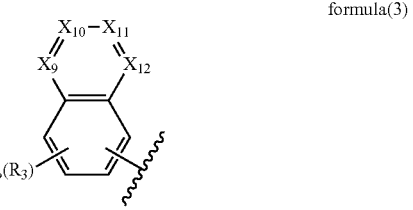

formula(4)
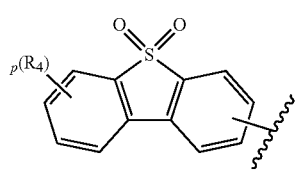

formula(5)
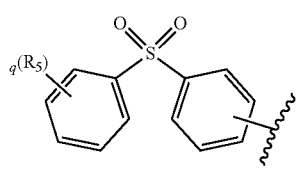

formula(6)
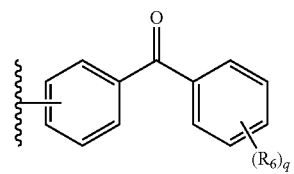

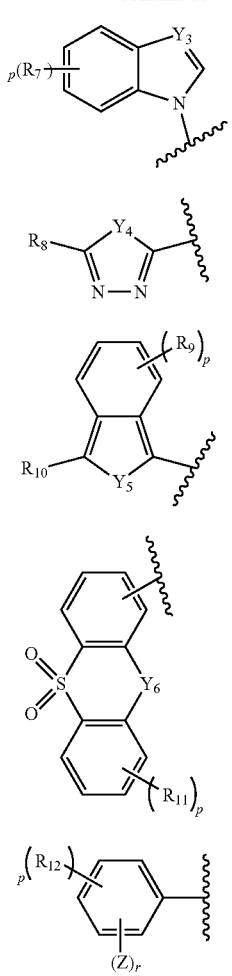

formula(7)

formula(8)

formula(9)

formula(10)

formula(11)

L₁ and L₂ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, $Y_1$ to $Y_3$ is a CH group, $Y_4$ to $Y_6$ is a divalent bridge selected from the atom or group consisting from O, S, C($R_{13}$)($R_{14}$), $NR_{15}$, and Si($R_{16}$)($R_{17}$); $X_1$ to $X_{12}$ represent a nitrogen atom or C($R_s$), and each Rs represents a hydrogen, a phenyl, a substituted or unsubstituted alkyl group having 1 to 30 carbon atoms, and a substituted or unsubstituted aryl group having 6 to 30 carbon atoms; Z represents a cyano group, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

2. An organic electroluminescence device comprises a pair of electrodes consisting of a cathode and an anode, and between the pairs of electrodes comprise at least a light emitting layer, and one or more layers of organic thin film layer, wherein the light emitting layer or organic thin film layer comprises the organic compound with a general formula (1) according to claim 1.

3. The organic electroluminescence device according to claim 2, wherein a difference between a singlet energy of the organic compound and a triplet energy of the organic compound is less than 0.25 eV.

4. The organic electroluminescence device according to claim 2, wherein the organic compound is a delayed fluorescence compound.

5. The organic electroluminescence device according to claim 2, wherein the organic compound with a general formula (1) is a delayed fluorescence host material.

6. The organic electroluminescence device according to claim 2, wherein the organic compound with a general formula (1) is a delayed fluorescence dopant material.

7. The organic electroluminescence device according to claim 2, wherein the light emitting layer comprises a dopant material.

8. The organic electroluminescence device according to claim 2, wherein the light emitting layer comprises a host material.

9. The organic electroluminescence device according to claim 2, wherein the organic compound with a general formula (1) is a phosphorescent host material.

10. The organic electroluminescence device according to claim 2, wherein the organic compound with a general formula (1) is a hole blocking material.

11. The organic electroluminescence device according to claim 2, wherein the organic compound with a general formula (1) is an electron transporting layer(ETL) material.

12. The organic electroluminescence device according to claim 2, wherein the device is an organic light emitting device.

13. The organic electroluminescent device according to claim 2, wherein the device is a lighting panel.

14. The organic electroluminescent device according to claim 2, wherein the device is a backlight panel.

15. An organic compound represented by the following formula (12):

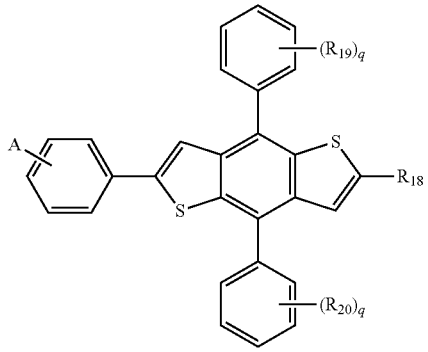

formula (12)

wherein $A_1$ is an acceptor represented from formula (2) to formula (11)

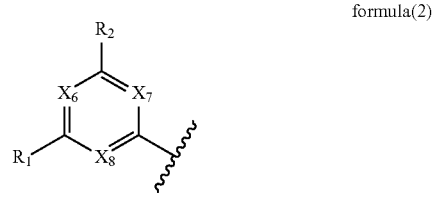

formula(2)

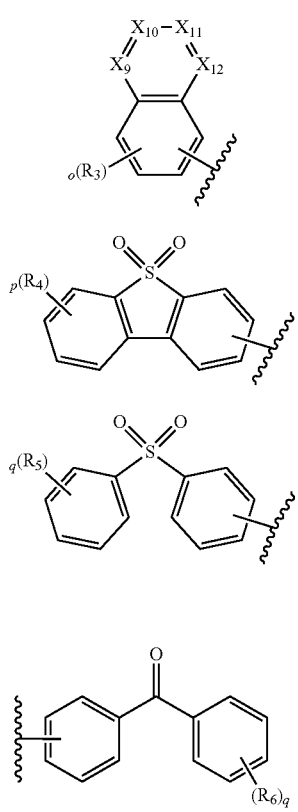

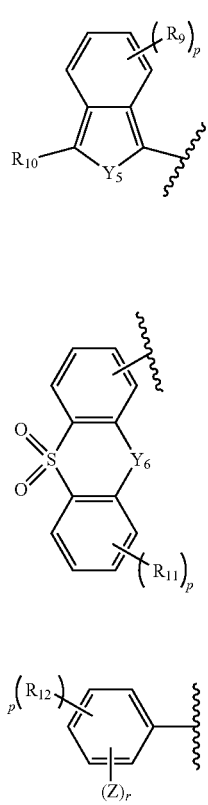

L₁ and L₂ represent a substituted or unsubstituted divalent arylene group having 6 to 30 ring carbon atoms, m and n represent an integer of 0 or 1; m and n cannot be 0 simultaneously, o represents an integer of 0 to 3, p represents an integer of 0 to 4, q represents an integer of 0 to 5, r represents an integer of 1 to 5, Z is represents a cyano group, $R_1$ to $R_{12}$ and $R_{18}$ to $R_{22}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

16. An organic compound represented by one of the following:

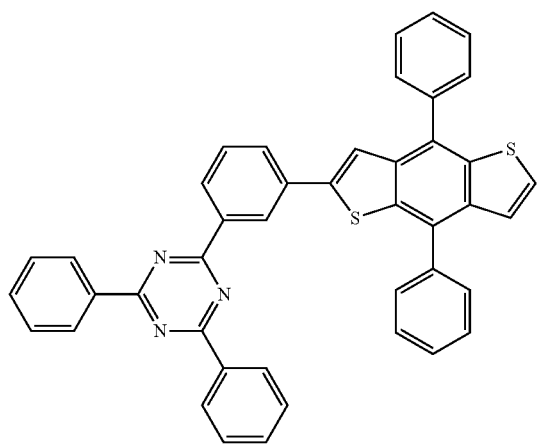

-continued
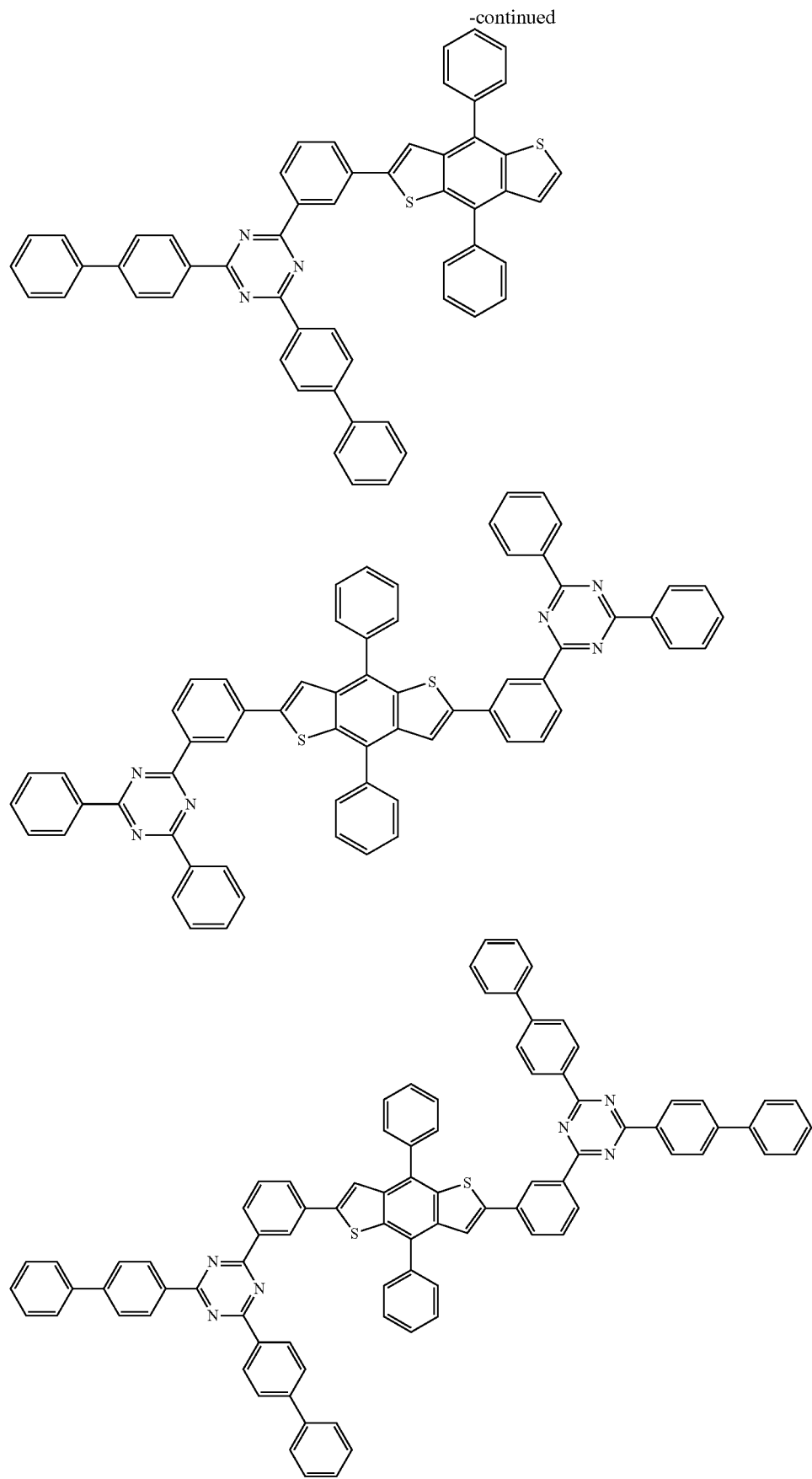

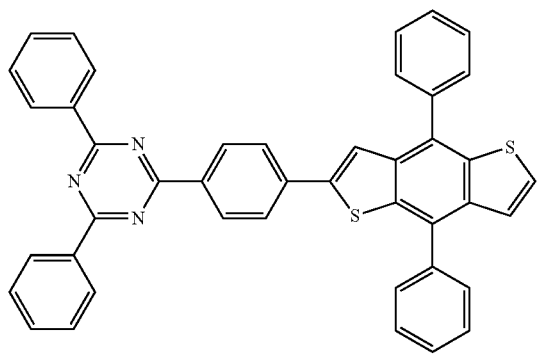
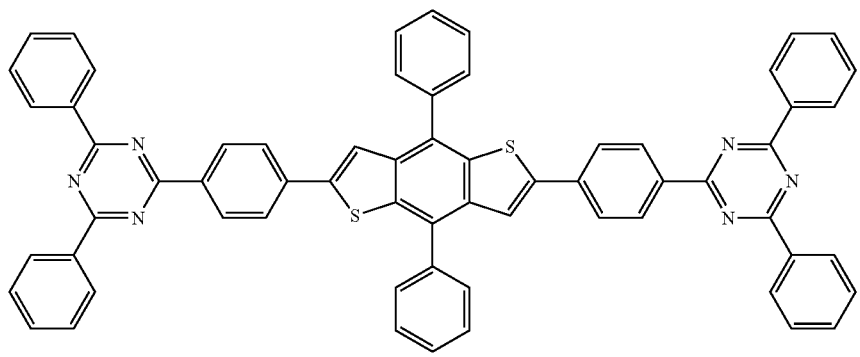
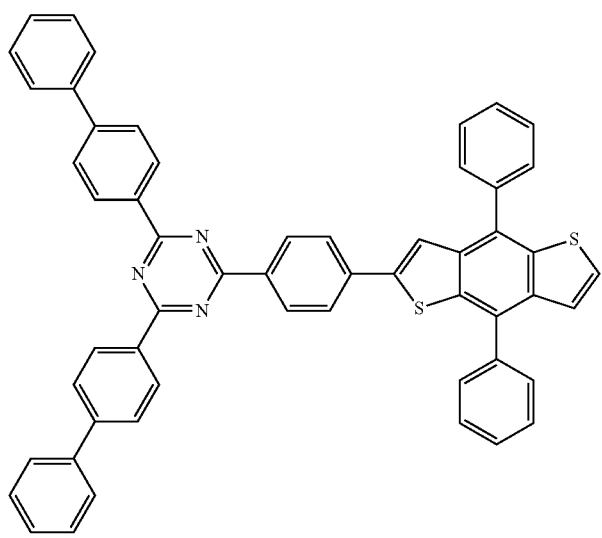

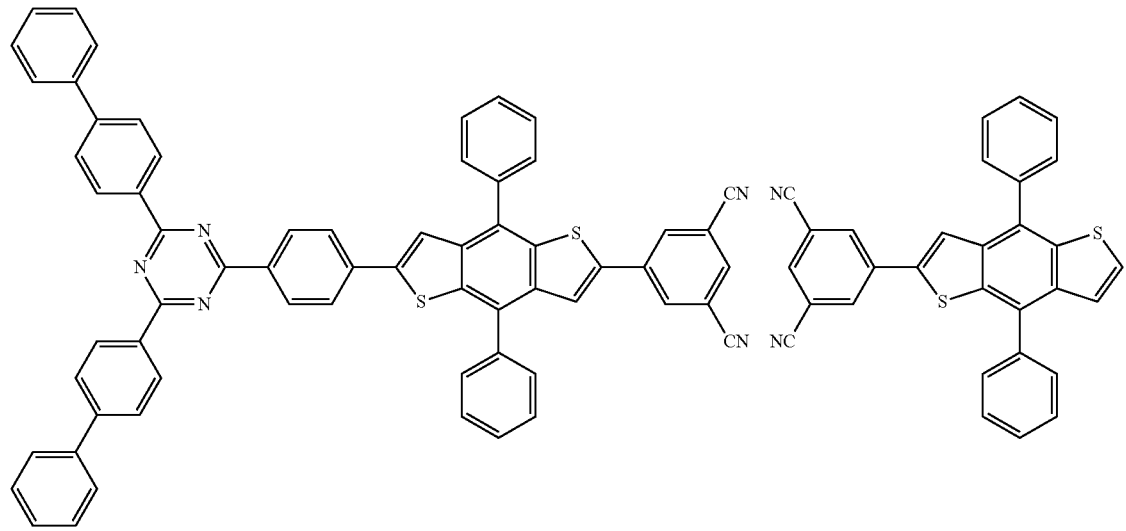
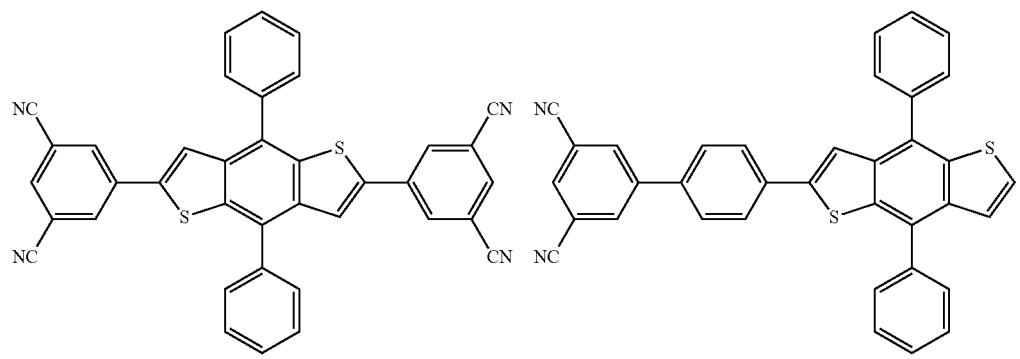
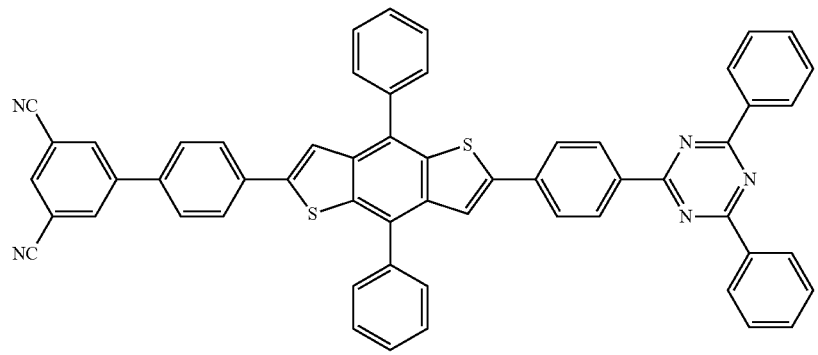
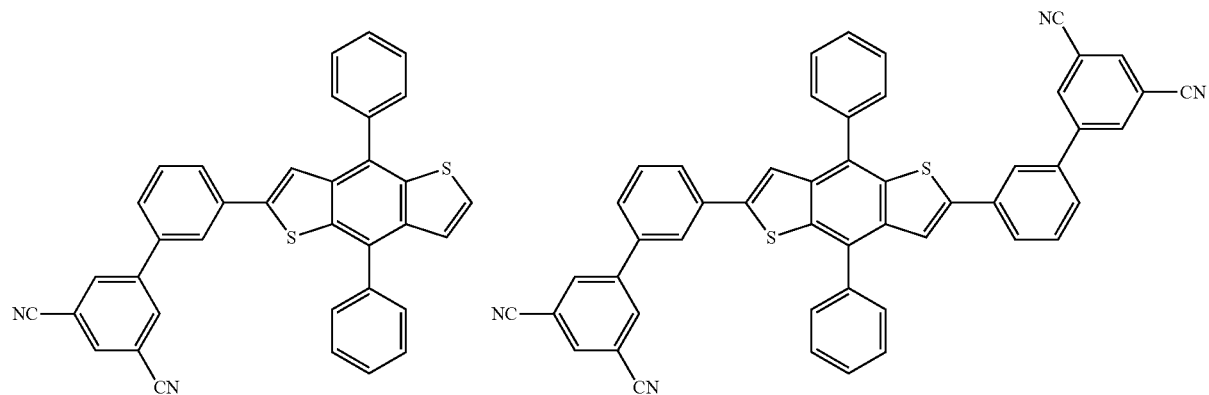

-continued
59
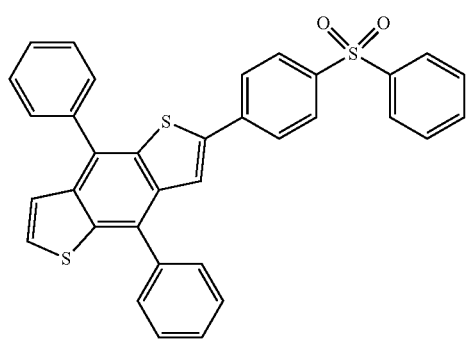
60
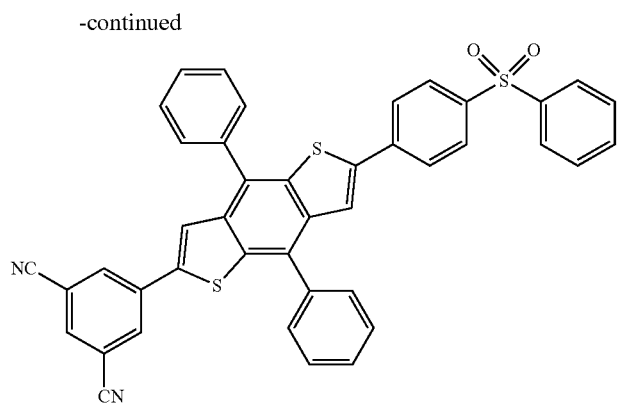
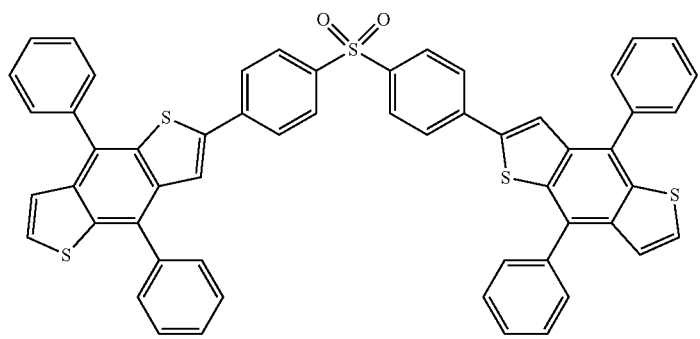
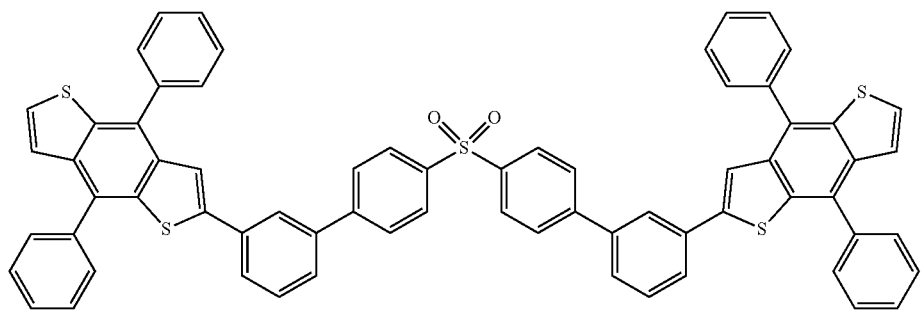
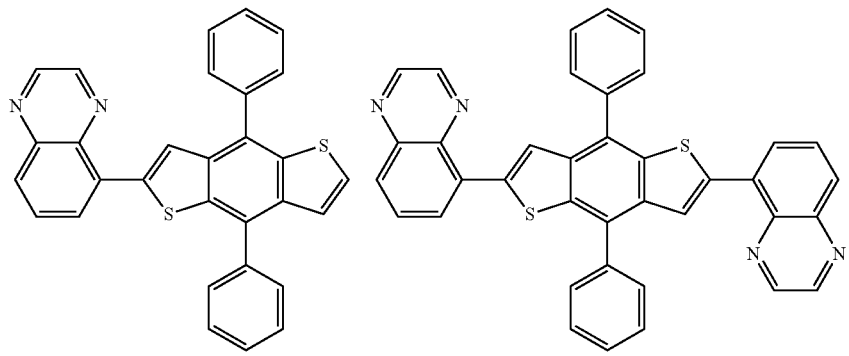

-continued
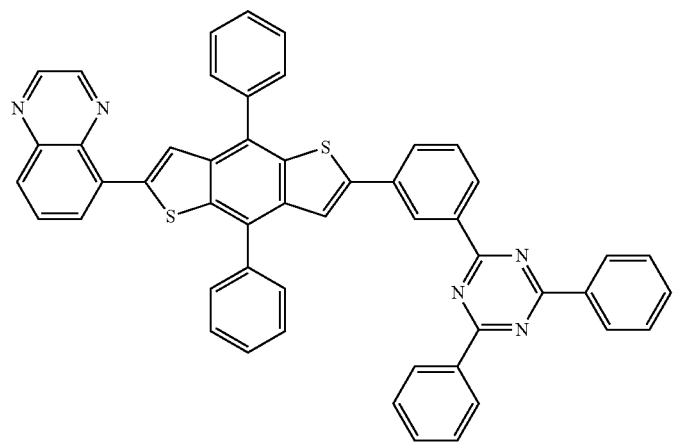
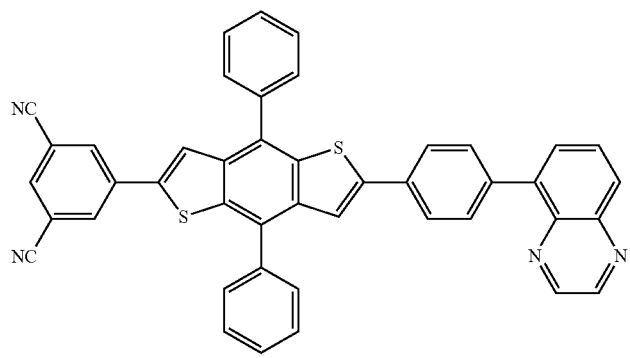
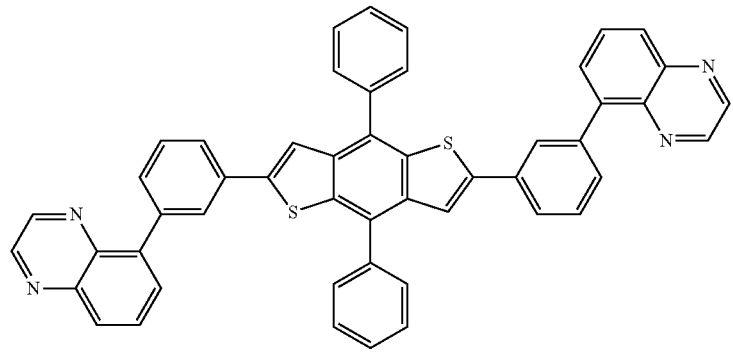
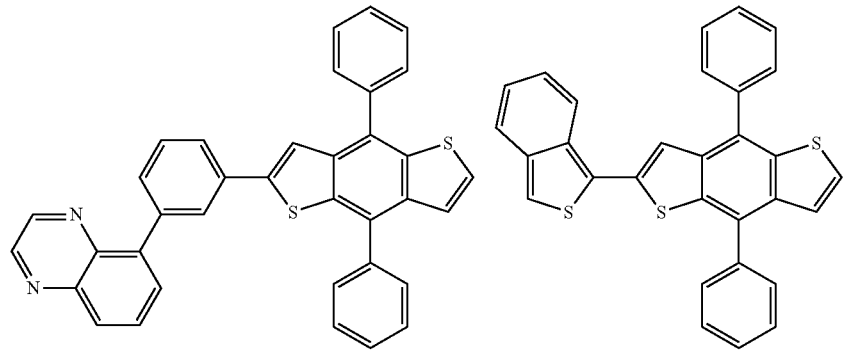

-continued
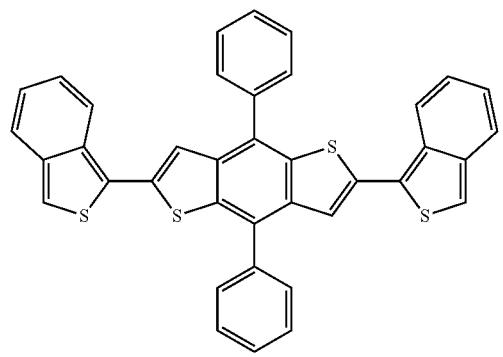
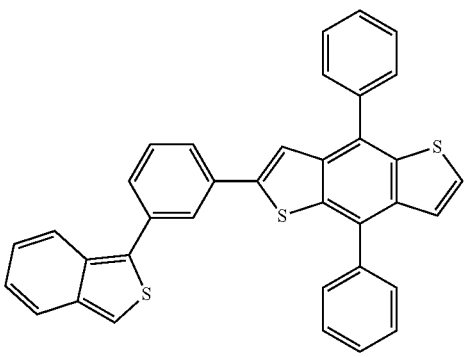
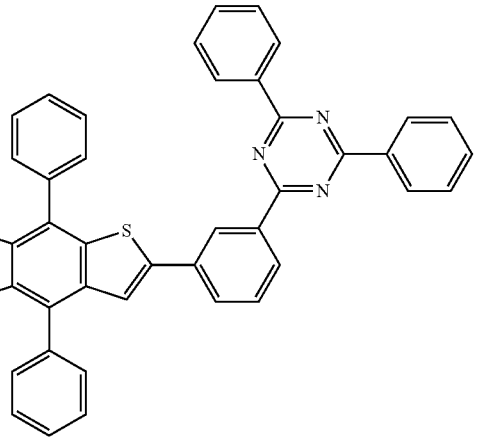
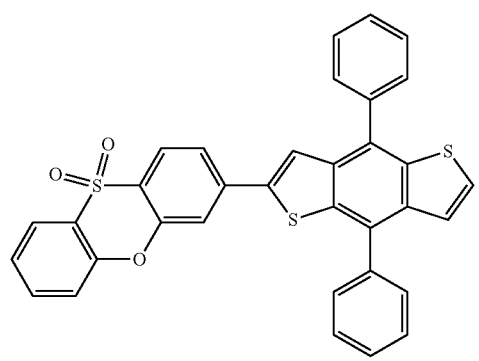
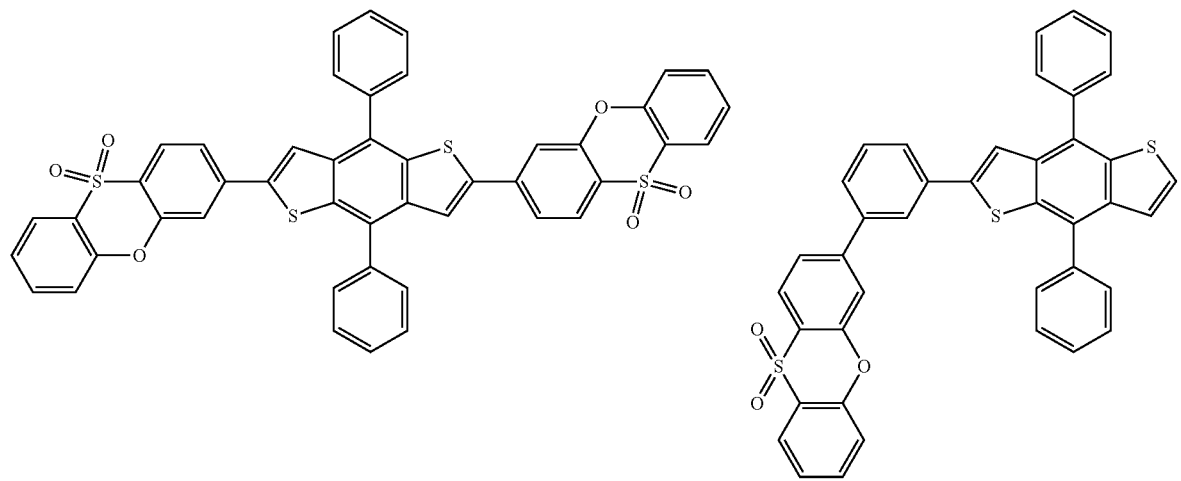

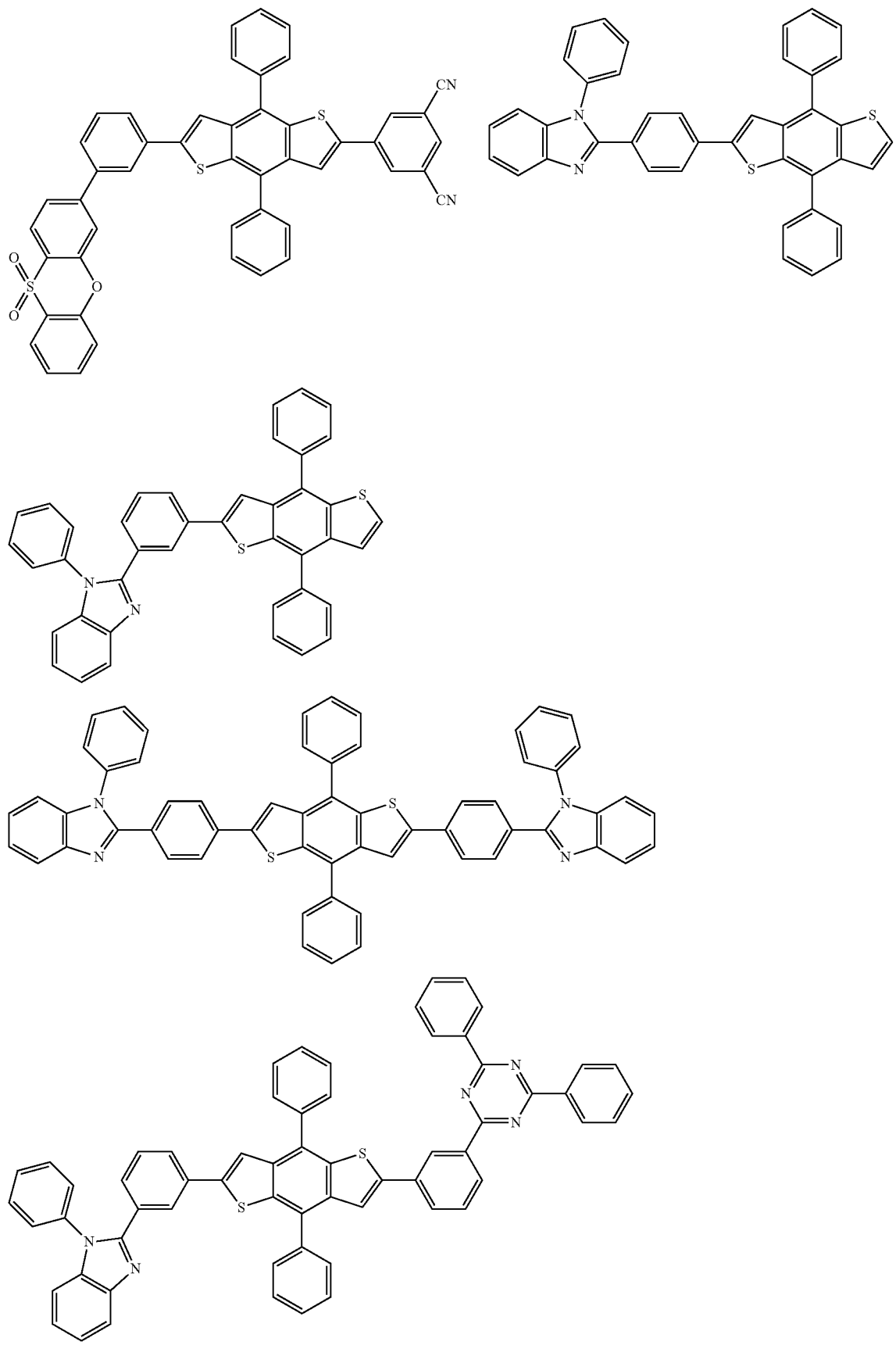

-continued
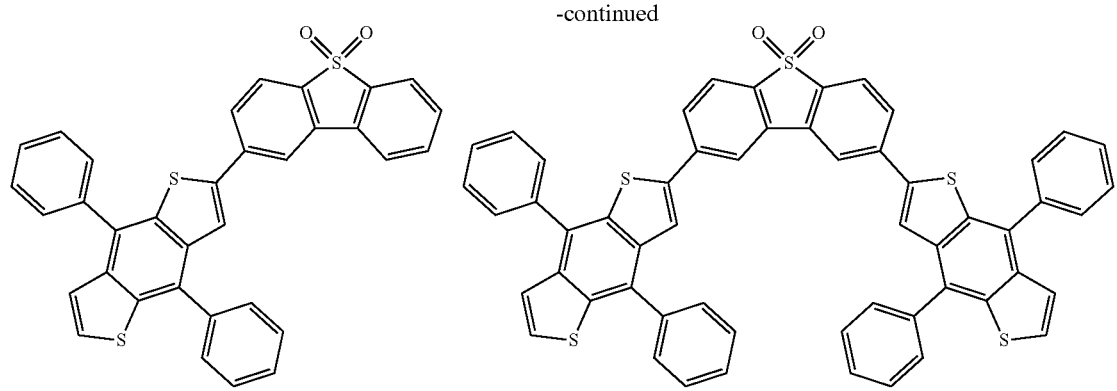
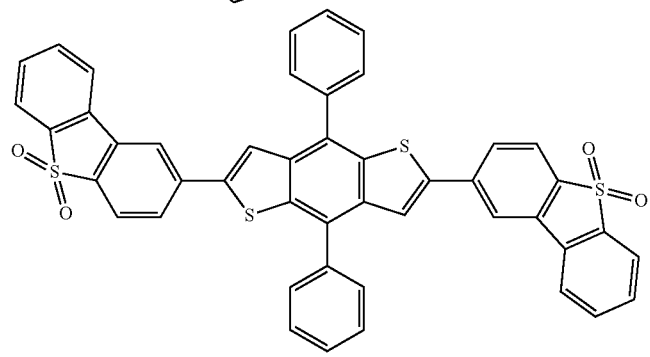
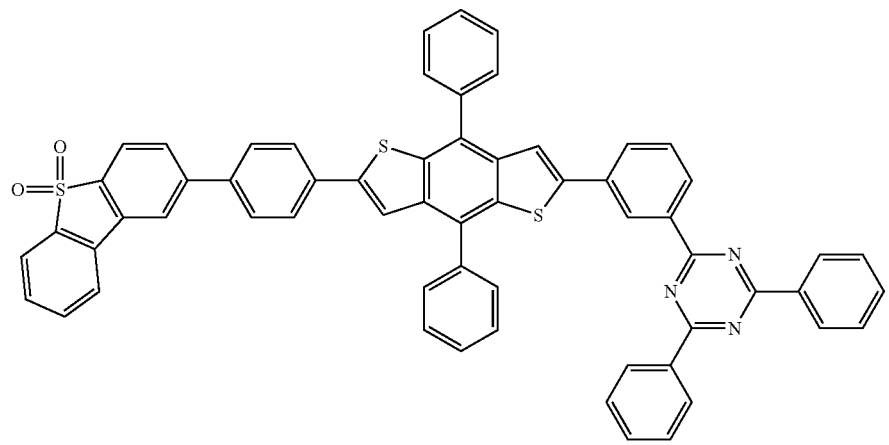
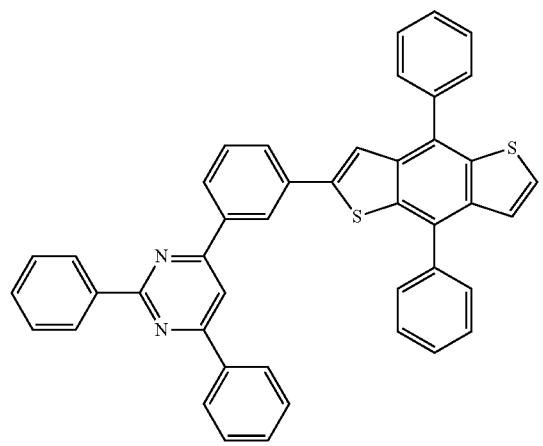

-continued
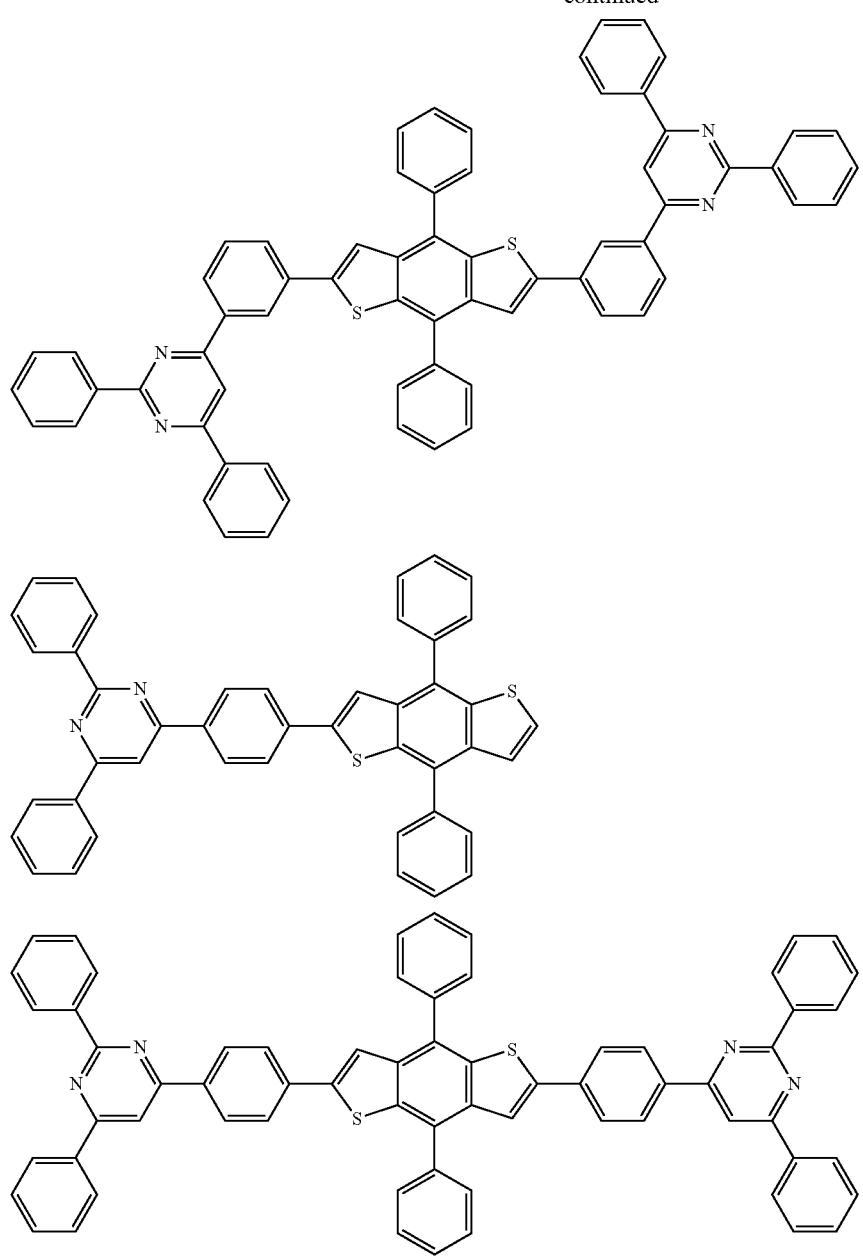
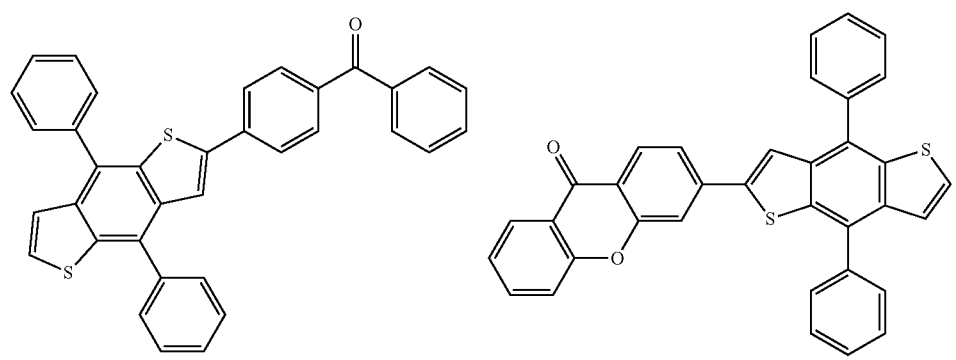

-continued
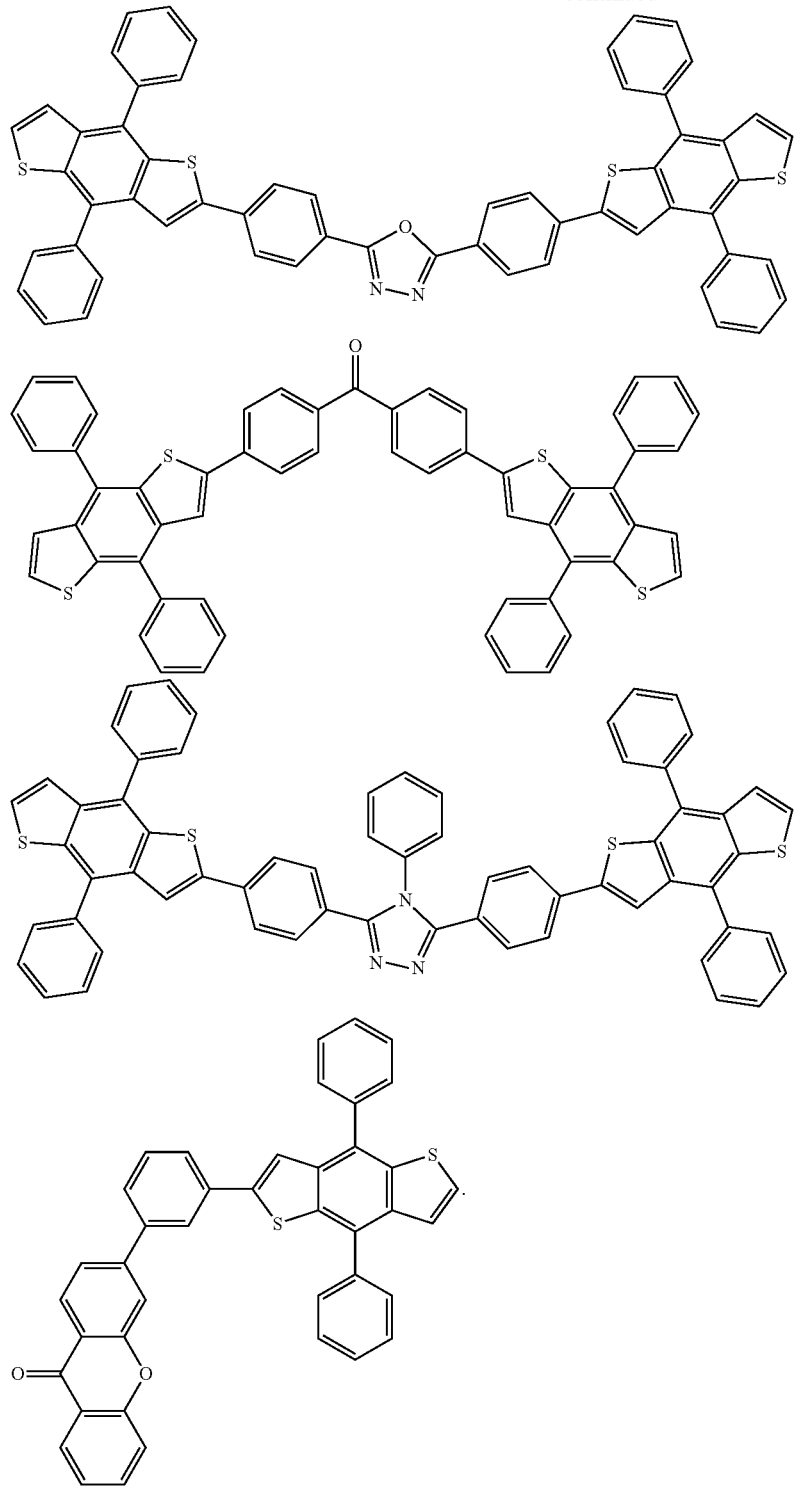
* * * * *